United States Patent [19]

Tomba et al.

[11] Patent Number: 5,531,678
[45] Date of Patent: Jul. 2, 1996

[54] METHOD OF USING A SPRING-LOADED RECIPROCABLE STYLET HOLDER TO EJECT A T-FASTENER

[75] Inventors: Todd C. Tomba, Dublin; Edgar G. Manosalva, Worthington; Donald J. Goldhart, Grove City, all of Ohio; James D. Morrow, Oak Park, Ill.

[73] Assignee: Abbott Laboratories, Abbott Park, Ill.

[21] Appl. No.: 422,297

[22] Filed: Apr. 14, 1995

Related U.S. Application Data

[62] Division of Ser. No. 308,242, Sep. 19, 1994.

[51] Int. Cl.[6] .................................................. A61M 31/00
[52] U.S. Cl. .............................. 604/51; 128/898; 606/215
[58] Field of Search .......................... 604/49, 175, 51–53, 604/280–283, 264, 272, 171, 49, 131, 134–136, 160, 161, 158, 164, 165, 167, 170, 11, 13, 15, 16; 606/108, 215, 220; 600/37; 128/898, 899

[56] References Cited

U.S. PATENT DOCUMENTS

| | | | |
|---|---|---|---|
| Re. 34,021 | 8/1992 | Mueller et al. | 604/51 |
| 2,751,907 | 6/1956 | Hickey. | |
| 5,151,086 | 9/1992 | Duh et al. | 604/51 |
| 5,307,924 | 5/1994 | Manosalva et al. . | |
| 5,318,543 | 6/1994 | Ross et al. | 604/164 |
| 5,341,823 | 8/1994 | Manosalva et al. | 128/898 |

FOREIGN PATENT DOCUMENTS 0076239  4/1983  European Pat. Off. .

Primary Examiner—Randall L. Green
Assistant Examiner—Ronald K. Stright, Jr.
Attorney, Agent, or Firm—Brian R. Woodworth

[57] ABSTRACT

A spring-loaded reciprocable stylet holder assembly includes a cap; a hollow body element partially nested within and reciprocable a major part of its length into the cap; a spring urging the body element outwardly of the cap; and a stylet supported at one end by the cap and extending through and beyond the body element. The remote end of the body element has a small borehole through which the stylet extends. The remote end is also provided with attachment means for a hypodermic needle with slotted tip for T-fastener emplacement, the needle telescopically surrounding the full length of the stylet. In a useful modification of the device an insufflation adapter having a side port for attachment of a hypodermic syringe is placed in line between the body element and the hypodermic needle. The stylet holder assembly with a slotted hypodermic needle attached thereto may be used for emplacing a T-fastener in a hollow organ of a person, such as the stomach.

2 Claims, 22 Drawing Sheets

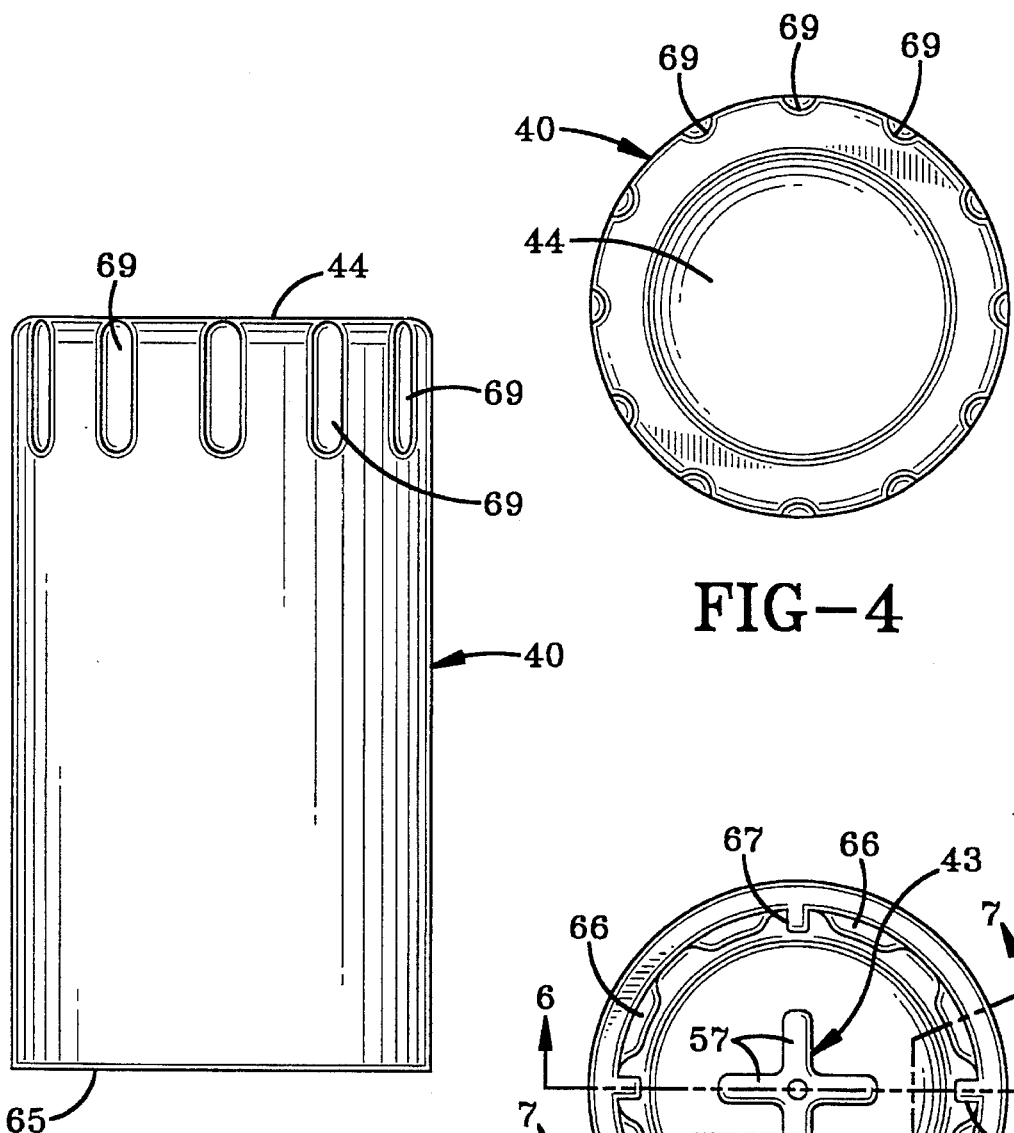

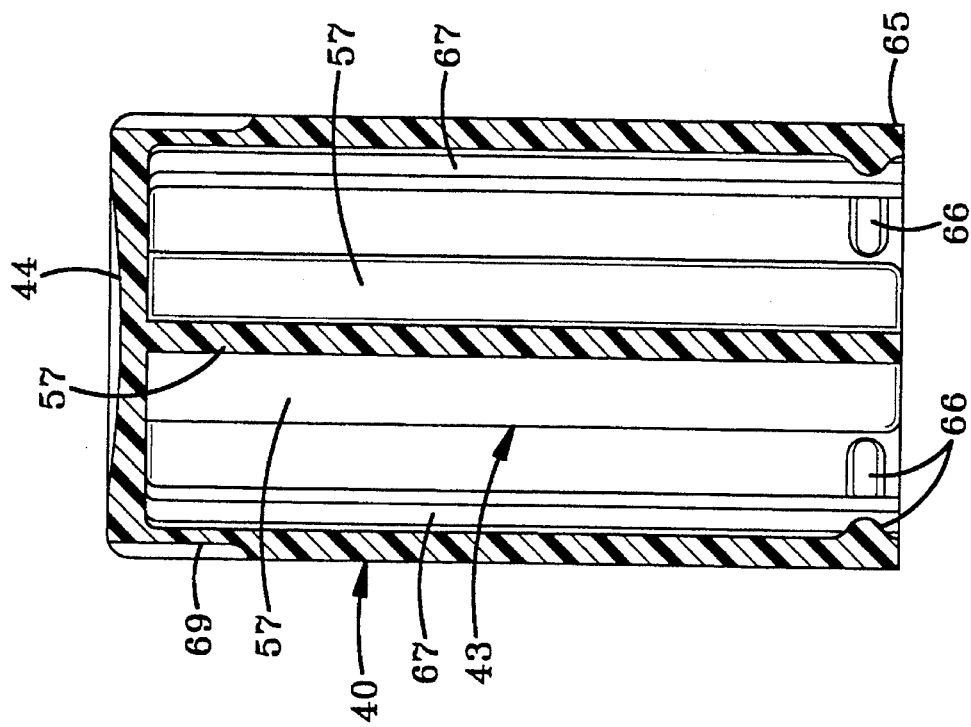
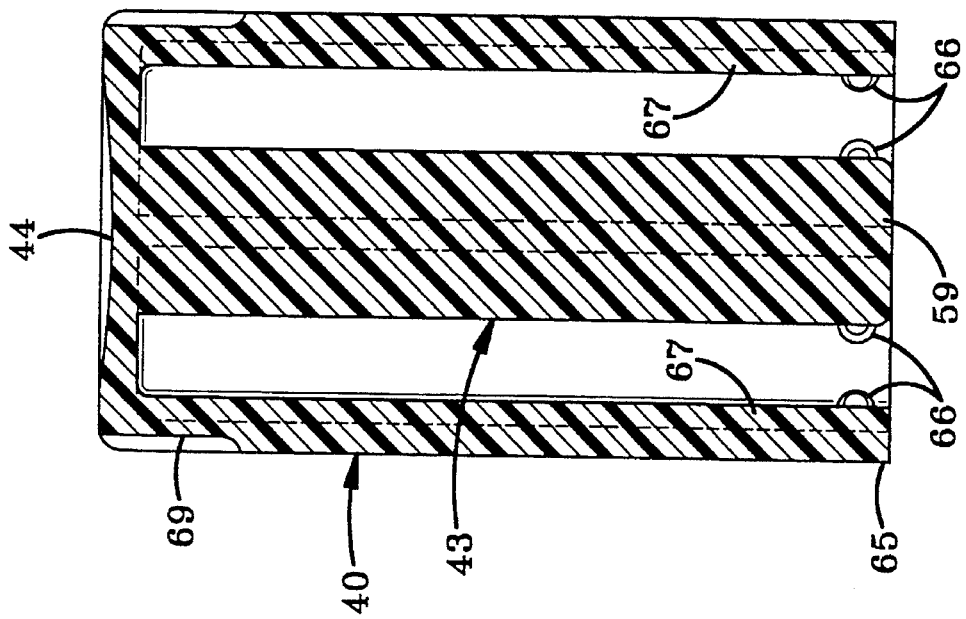
FIG-7
FIG-6

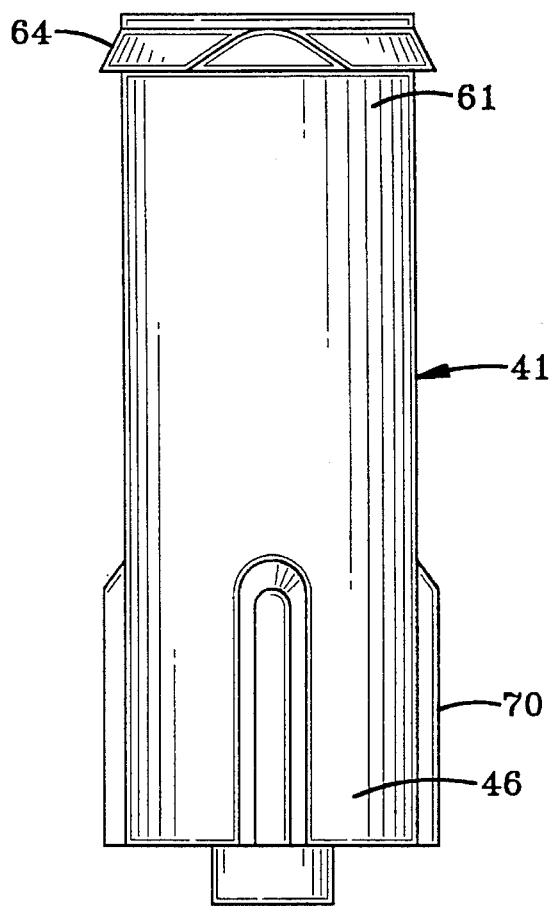
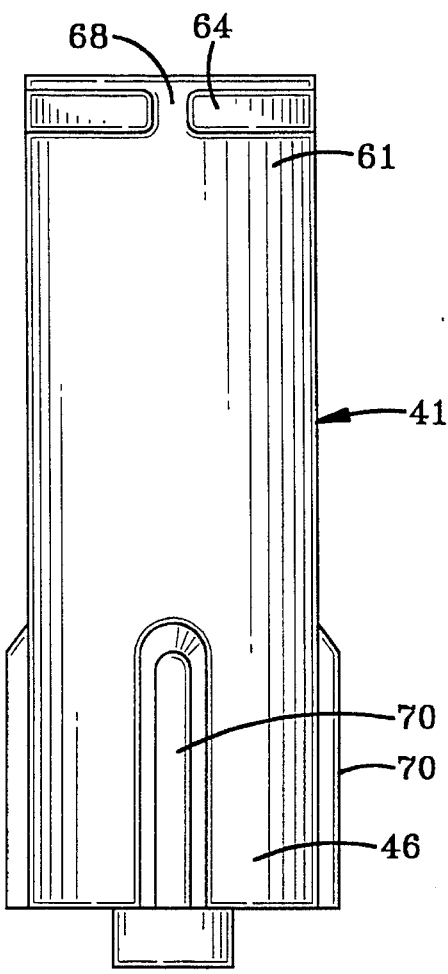
FIG-8    FIG-9
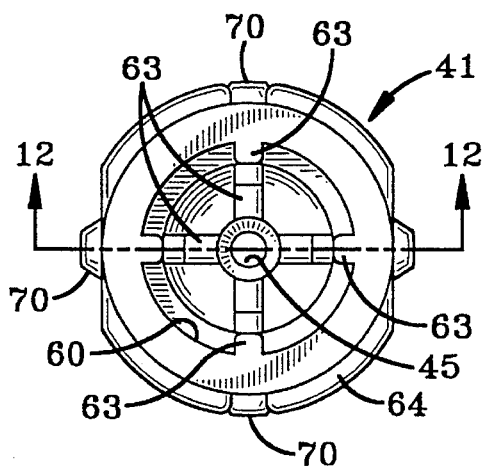
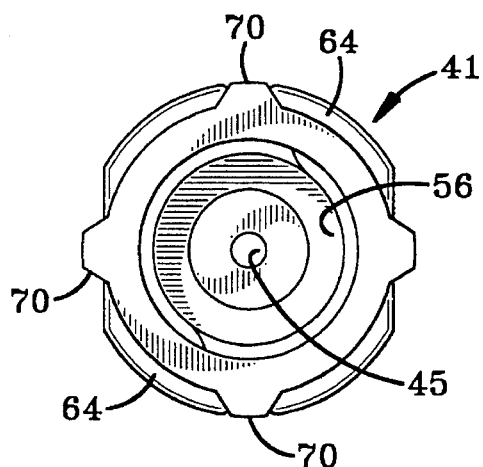
FIG-10    FIG-11

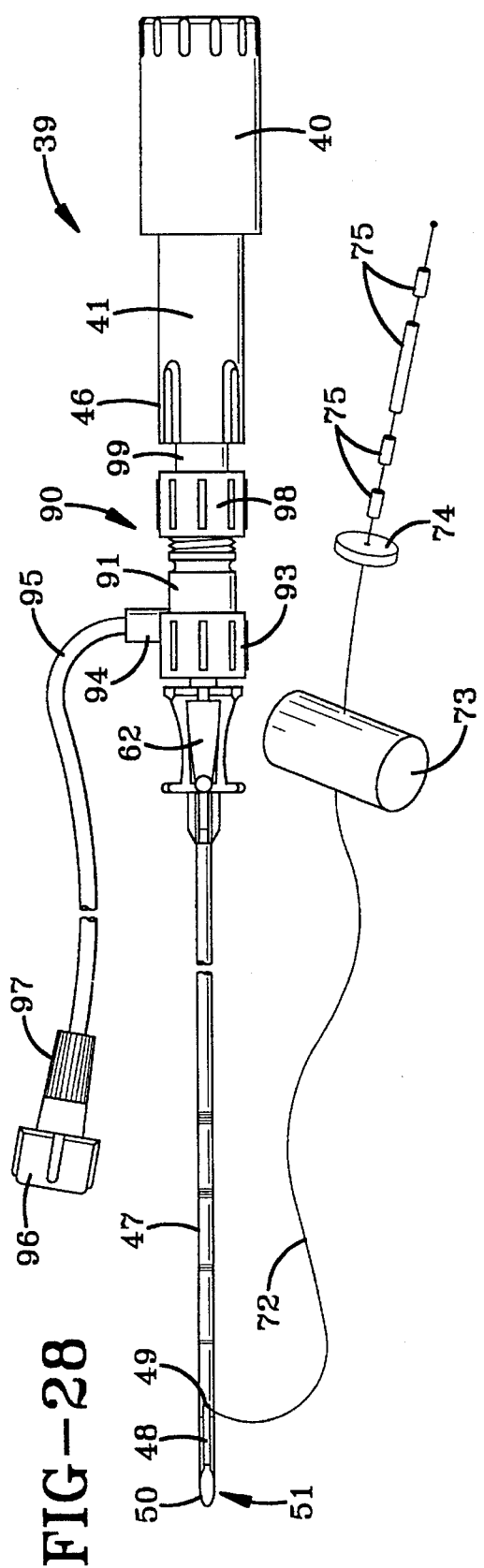
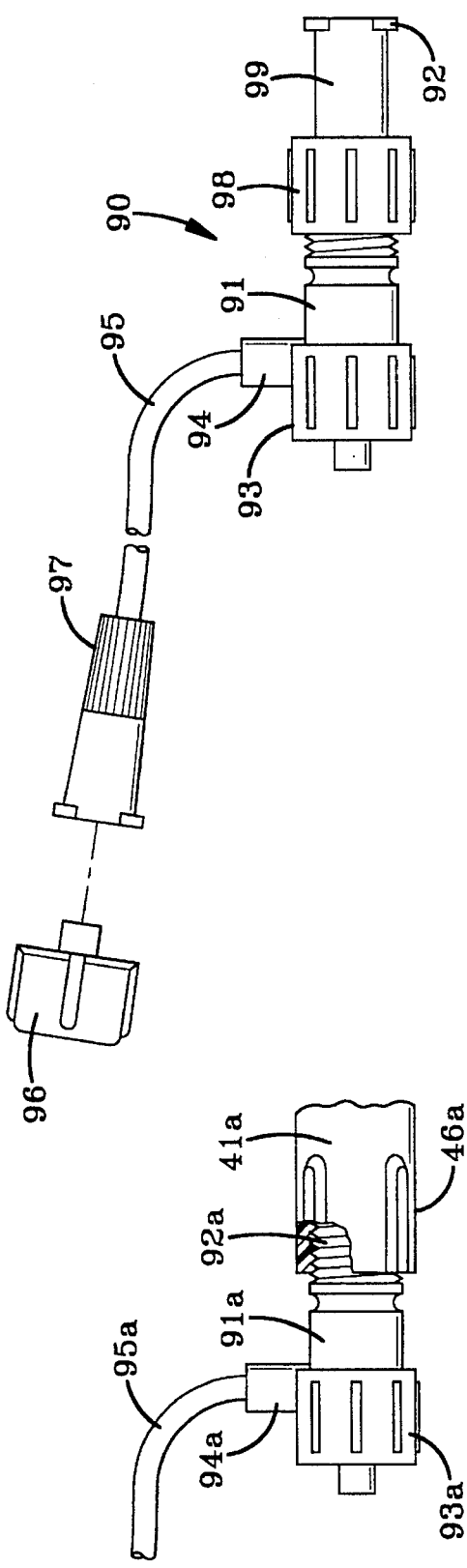

METHOD OF USING A SPRING-LOADED RECIPROCABLE STYLET HOLDER TO EJECT A T-FASTENER

This application is a divisional of application Ser. No. 08/308,242 filed Sep. 19, 1994, pending.

FIELD OF THE INVENTION

The present invention relates to surgical instruments and more particularly to the use of T-shaped tension members in certain surgical procedures, and even more particularly to a device for conveniently holding and reciprocating a stylet used in controllably ejecting a T-shaped tension member from a slotted hypodermic needle during its emplacement in a surgical procedure.

BACKGROUND OF THE INVENTION

U.S. Pat. No. 34,021 discloses a method and apparatus for fixing a hollow organ of a patient to the body wall of the patient using T-shaped tension members, hereinafter referred to as "T-fasteners". Examples of surgical procedures which may utilize the teachings of U.S. Pat. No. 34,021 are the securing of a patient's stomach or bowel in apposition to the abdominal wall during a gastrostomy or jejunostomy procedure. These procedures are performed to facilitate the insertion of a feeding tube through the abdominal wall directly into the stomach or bowel. Examples of individuals who may require securing of the stomach or bowel in apposition to the abdominal wall in order that a feeding tube may be installed include burn patients, whose daily caloric needs are high; critically ill, weak or comatose patients with a traumatized esophagus, who may be unable to swallow food. Increasingly, a new class of persons requiring such treatment include patients infected with the HIV virus.

A relatively new method of placing a gastrostomy tube or jejunostomy tube is described in U.S. Pat. No. 5,151,086. In this patent, a laparoscopic procedure is described which utilizes instruments and equipment which pass through the skin and the tissue of the body wall at the surgical site and to the hollow organ to be penetrated. The laparoscopic procedure requires the handling and use of many instruments and supplies including a nasogastric tube, a scalpel, needles, syringes, T-fasteners, a J-guide wire, dilators, a gastrostomy tube or a jejunostomy tube, a stylet and water soluble lubricant. In the procedure described herein as well as in U.S. Pat. No. 5,151,086, each T-fastener is inserted into a slotted, hollow needle to facilitate placement within the hollow organ. Care must be taken to avoid ejecting the T-fastener prematurely before it is properly emplaced, or else it will be wrongly placed within the patient, or, if outside the body of the patient, it will likely fall onto a non-sterile surface and have to be discarded. Considering the number of items that must be handled during such procedures it is evident that there is a need for a convenient apparatus and method of holding and controlling the stylet used to eject the T-fasteners from the slotted hypodermic needle used for emplacement.

SUMMARY OF THE INVENTION

In a first aspect of the invention there is provided a spring-loaded reciprocable stylet holder assembly having a cap with a closed end and an open end and a longitudinal axis; a hollow body element having a longitudinal axis, an open end portion partially nested within and reciprocable partially into the cap, and a substantially closed end, the longitudinal axes of the cap and body element being coincidental; a spring urging the body element outwardly of the cap; and a stylet supported at one end thereof by the cap, the stylet slideably extending through the body element along the longitudinal axis thereof and through a borehole in the closed end of the body element and well beyond the body element. Preferably, the cap and body element are both cylindrical and means is provided for retaining the body element in a telescoping reciprocal relationship with the cap, i.e., the body element is restrained from sliding completely out of the cap. It is further preferable to support the stylet from a post or plunger that depends within the cap from the closed end thereof to about the open end and is reciprocable into and out of the hollow cylindrical body element. It is also preferred to use a coil spring as the spring urging the body element out of the cap and from around the plunger, and, it is preferred to position the coil spring around the plunger and substantially coextensively therewith.

In a further aspect of the invention the distal end of the body element is provided with means for attachment of a hypodermic needle for the emplacement of a T-fastener, the attachment means being, usually, the female portion of a conventional luer lock fitting. The stylet extends through the assembly, including the attachment means, and the needle is attached so as to telescopically cover the stylet. With a needle of the requisite gauge mounted to the luer lock, and having the tip, proximal to the beveled end and contiguous thereto, slotted to receive a T-fastener for use in insertion thereof, and with the needle and the stylet being each of an appropriate length so that in the assembly the stylet is extendible, by manipulation of the holder, to the lower, or distal, end of the slot, there is provided apparatus ready to be loaded with a T-fastener for emplacement of the same in the stomach or bowel of a patient in a surgical procedure.

In a further aspect of the invention, an insufflation adapter with a T-connection is placed in-line, i.e., in series, between the needle attachment means of the body element of the present stylet holder and the needle in the assembly for emplacement of a T-fastener, thus providing means for injecting into or withdrawing from a hollow organ of a patient any appropriate fluid, i.e., liquid or gas, without disconnecting the assembly.

Preferably the insufflation adapter comprises a body portion with a passageway formed therethrough and a hemostasis valve in the passageway, and complementary luer lock fittings at each end, the body portion having a laterally projecting T-connection communicating with the passageway distal to the hemostasis valve and having a flexible tubing extension terminating in a female fitting for connecting to a syringe, such as a luer lock fitting, and a fluid-tight closure for the luer lock fitting, such as a complementary screw-on cap, thus facilitating insufflation as may be desired or needed during the procedure of emplacing T-fasteners.

In another aspect of the invention a novel method of controllably holding and ejecting a T-fastener from a hypodermic needle tip during placement in a hollow organ of a patient comprises:

providing an assembly of the spring-loaded reciprocable stylet holder of the invention including a stylet mounted therein, and equipped with means for attaching a hypodermic needle to the distal end of the body element thereof, and a hypodermic needle held by the attachment means with the stylet extending therethrough to adjacent the tip thereof, the needle being of the requisite gauge and length for insertion of a T-fastener within a hollow organ of a patient and having a slotted tip portion to slideably receive and hold a T-fastener;

placing a T-fastener with an attached filament, ordinarily a suture, within the slot of the needle with the distal end of the stylet resting within the needle closely adjacent the T-fastener;

inserting the needle into a hollow organ of the patient at a pre-selected site;

sufficiently pressing down the cap of the stylet holder over the body element and against the urging of the spring within the stylet holder to move the stylet to eject the T-fastener from the tip of the needle; and withdrawing the assembly of the stylet holder and the needle from the body of the patient.

Preferably the filament is attached to the T-fastener at about the mid-length of the fastener and the filament is grasped along with the stylet holder during insertion of the needle, and when the assembly of stylet holder and needle is withdrawn from the body of the patient, retaining means are applied to the filament outside the body while the filament is held under tension to position the body organ.

BRIEF DESCRIPTION OF THE DRAWINGS

FIG. 3 is a slightly enlarged side view of the cap of the stylet holder assembly shown in FIG. 1;

FIG. 4 is a top, or plan, view of the cap shown in FIG. 3;

FIG. 5 is a bottom view of the cap shown in FIG. 3;

FIG. 6 is a view of the cap in longitudinal section taken along the diametric line 6—6 of FIG. 5;

FIG. 7 is a view of the cap in longitudinal section taken along the modified diametric line 7—7 of FIG. 5;

FIG. 8 is a slightly enlarged side view of the body element of the stylet holder assembly of FIG. 2;

FIG. 9 is a side view of the body element of FIG. 8, upon being rotated 90 degrees about its longitudinal axis from the view in FIG. 8;

FIG. 10 is a top, or plan, view of the body element of FIG. 9;

FIG. 11 is a bottom view of the body element of FIG. 9;

FIG. 28 is a side view of a modified form of an assembly according to the invention in which an insufflation valve within an adapter that serves as a valve body is placed in-line between the novel stylet holder assembly and the slotted needle for emplacement of a T-fastener, the insufflation valve body having a side "T" port with a short connecting piece of tubing with a luer lock fitting on the distal end closed with a cap; the adapter and its side connection providing for carrying out insufflation without disconnecting the stylet holder assembly;

FIG. 28A is a fragmentary view, partly broken away and in section, of a form of adapter for insufflation purposes which threadably connects to the body element of the stylet holder assembly instead of using a luer lock style connection, the body element having complementary internal threading formed therein the distal end thereof;

FIG. 29 is a side view of the adapter per se with appropriate male and female luer lock fittings for in-line attachment and with the cap closure, shown in exploded view, for the luer lock fitting at the free end of the tubing connected to the side "T" port. It should be understood that within the valve body shown in this view, as well as in FIG. 28A, there is a conventional hemostasis valve assembly with a borehole therethrough the axis thereof for passage of the stylet through to the needle, the valve being between the side "T" port and the attachment of the adapter to the body element.

BRIEF DESCRIPTION OF THE INVENTION

Figure 1:
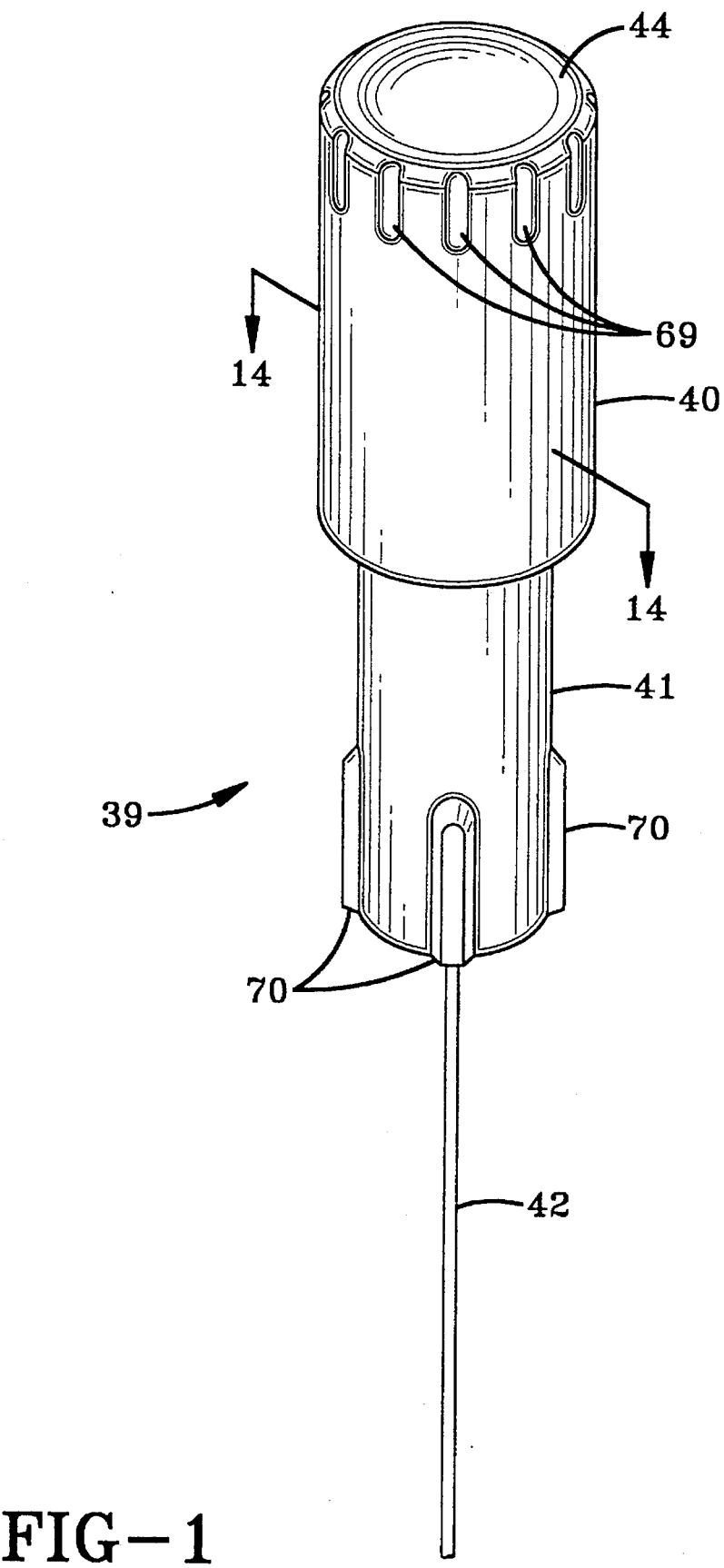
FIG. 1 is a perspective view of the stylet holder assembly of the invention.
Figure 2:
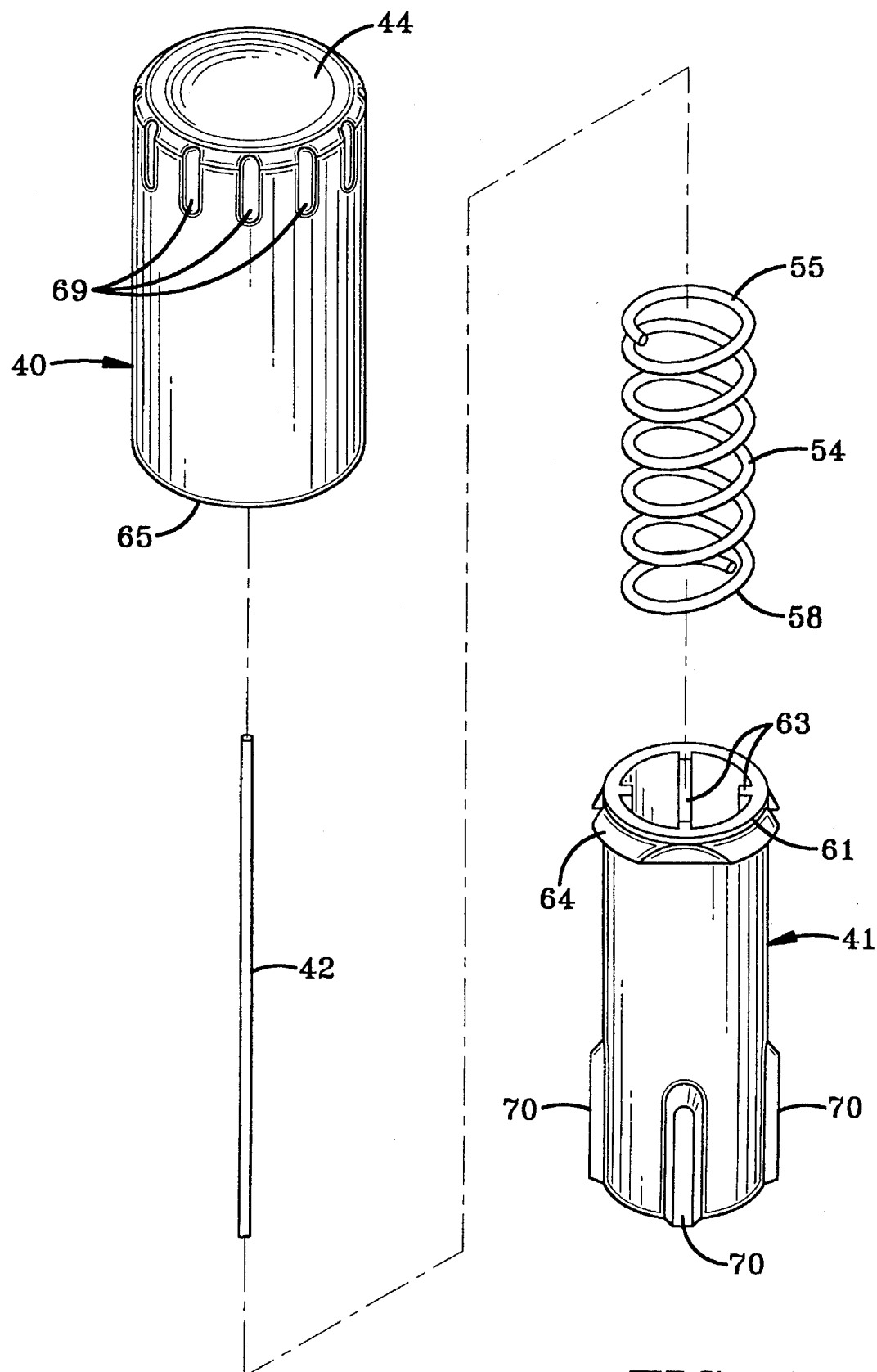
FIG. 2 is an exploded perspective view of the stylet holder assembly shown in FIG. 1.
Figures 15, 16:
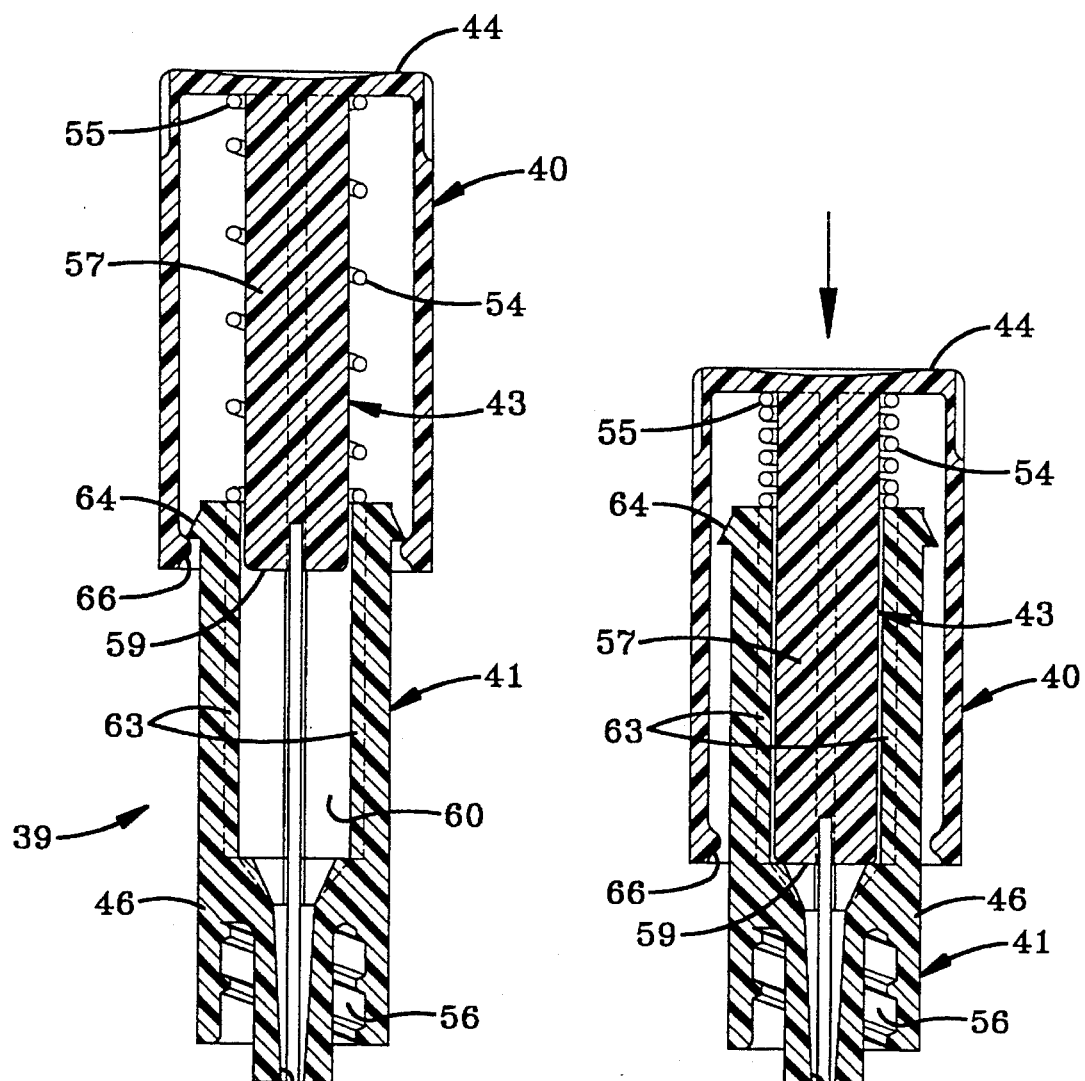
FIG. 15 is a view in longitudinal section taken along the modified diametric line 15—15 of FIG. 14.
FIG. 16 is a view in section similar to that of FIG. 15, but with the cap telescoped over the body element causing the stylet to be inserted further through the body element, and, the coil spring being compressed to permit the telescoping movement.

The various aspects of the invention will be better understood with reference to the drawings in which like parts are identified by like reference numerals. Referring now to FIGS. 1, 2 and 15, the stylet holder assembly of the invention, indicated generally by the reference numeral 39, is seen to consist mainly of a hollow cap 40 that telescopes slideably over a hollow body element 41. While both parts can be made with square or rectangular or oval cross-sections of appropriate complementary shape and dimensions, they will most conveniently be made round in section, i.e., both parts are cylindrical in nature. An elongated stylet 42, normally a thin metal rod, is supported by a post or plunger 43 extending axially within the cap 40 from the closed end 44 to about the full length of the cap, the stylet 42 extending in the axial direction from the plunger 43 and being cemented or otherwise attached thereto, or more usually, thereunto.

For the purposes of this description and the appended claims, it should be understood that the terms "distal" and "proximal" are taken with respect to the closed end 44 of the hollow cap 40 when the components of the stylet holder assembly are assembled in their operative configuration.

If desired, the plunger may be formed at its distal end with an axially bored hole or cavity into which an end of the stylet 42 is inserted and cemented thereto, or the hole may be tapped and the end of the stylet threaded and screwed into it. The plunger may be in the form of a cylindrical rod, preferably of a fluted nature, with longitudinal ridges or flanges that extend the length thereof, but more preferably takes the shape of at least three and up to about five, but usually four, elongated vanes or flange-like portions 57, each joined to the others by one elongated edge along a common axis with the flange-like portions about equi-angularly spaced about the common axis, and being integrally formed into a unit. Preferably, the plunger, when made with, for example, four flanges, is x-shaped, or star-shaped in section, the junction of the flanges, i.e., the longitudinal core of the plunger, being of relatively small diameter. Preferably the entire plunger is integrally formed with the cap and made of a polymeric resin or composition, such as, a high density polyethylene.

The stylet 42 extends axially along and through the hollow body element 41, when the body element and the cap 40 are assembled together for use, and out through an axial borehole 45 formed in the substantially closed end 46 of the body element. The substantially closed end 46 is shaped to provide attachment means for a slotted hypodermic needle used for emplacement of a T-fastener, such as the needle 47 used for the T-fastener 48 shown in FIG. 17. Usually the distal portion of the closed end 46 of the body element 41 is shaped as the female portion of a conventional luer lock fitting, such as the cavity 56 shown in section in FIGS. 12, 15 and 16, so that the substantially closed end 46 receives, in locking relationship, a conventional needle hub, such as needle hub 62 shown in FIG. 17, which is the male portion of a luer lock fitting.

Figure 17:
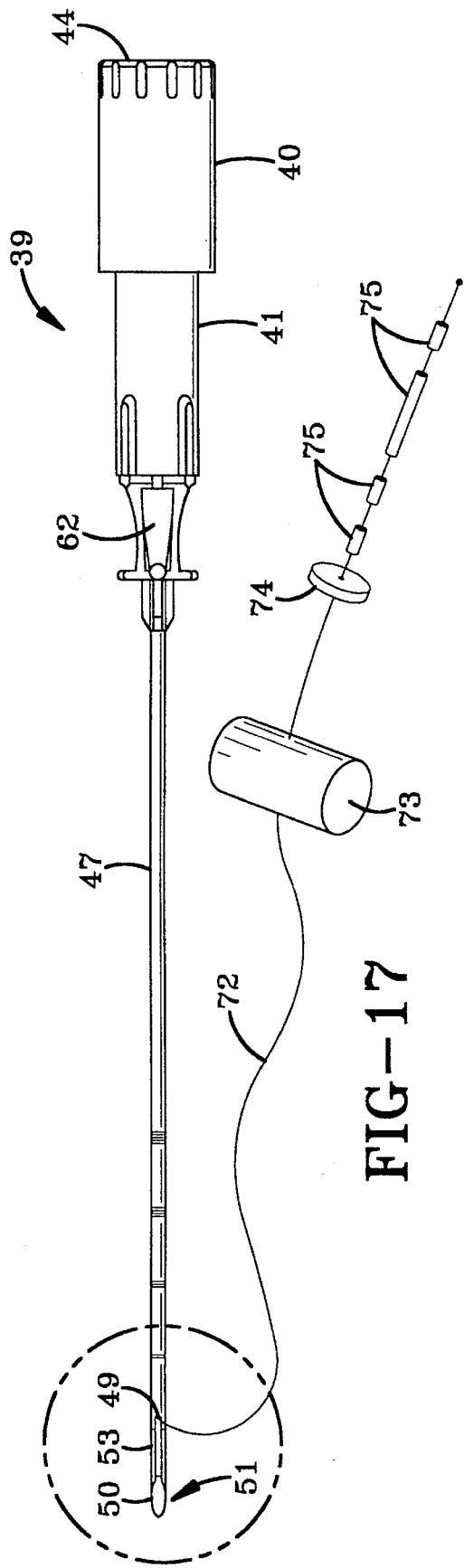
FIG. 17 is a side view of the stylet holder assembly of the invention with a slotted hypodermic needle attached at the luer lock fitting and with a T-fastener positioned in the needle with one-half of the T-fastener visible in the slot at the beveled tip of the needle with a filament extending from the T-fastener as part of a T-fastener assembly, including a pledget, a washer and retaining-crimping elements, not yet crimped, threaded onto the filament.
Figure 17A:
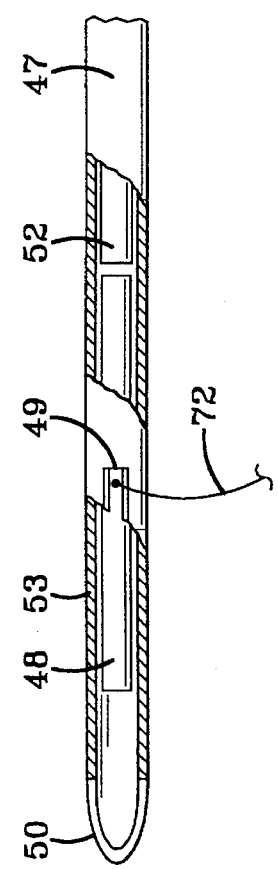
FIG. 17A is an enlarged fragmentary view of the portion of the assembly encircled in FIG. 17, illustrating details of the beveled needle tip and the T-fastener and the adjacent distal end of the stylet, the T-fastener being lodged in the needle with half of it visible in the slot of the needle, the slot extending from the proximal edge of the beveled portion, and the filament extending from the T-fastener next to the proximal end of the slot.

It is essential, as will be evident upon referring to FIGS. 17 and 17A, that when a needle is mounted on the stylet holder assembly 39 the stylet 42 extend to, or substantially to, the proximal edge 49 of the slot in the slotted portion 53 of the needle extending upwardly from the beveled portion 50 of the needle tip 51, in order that the distal end 52 of the stylet be in position to eject a T-fastener, such as T-fastener 48 slideably held in the slotted portion 53 of the needle 47, upon the cap 40 being pressed to telescope over the body element 41, thus thrusting the post 43 part way through the body element 41 and the stylet 42 carried by the post 43 being thrust further through the needle 47. It may be perceived readily that the distal end 52 of the stylet 42 must be close enough to the slotted portion 53 of the needle 47, and especially to the proximal end of a T-fastener 48 loaded into the slotted portion, in the assembled apparatus, so that the range of reciprocation of the cap 40 over the body element 41 will permit ejection of a T-fastener 48 held in the tip end of the needle right next to the beveled portion, half within the slotted portion 53 of needle 47, and half further into the needle than the closed end 49 of the slot.

Referring to the exploded view of the stylet holder assembly in FIG. 2 and the views in section, FIGS. 15 and 16, it is seen that spring means 54 is used to urge the body element 41 outwardly of nesting within the cap 40. Such a spring is needed in order to support the stylet 42 in the assembly 39 slightly above any T-fastener 48 inserted temporarily into the slotted portion 53 of the needle 47, until the surgeon using the assembly is ready to eject the T-fastener, as in placement thereof within the hollow organ of a patient. As shown, a coil spring is preferred, such as coil spring 54. Coil spring 54, of an appropriate diameter to slide readily over plunger 43 and its longitudinal flanges 57, is positioned with the proximal end 55 of the spring bearing up against the closed end 44 of the cap 40, and with the other, i.e., distal, end 58 of the spring close to the free end 59 of the post 43. For stable, uniform operation, the cavity 60 of the body element 41 must be of sufficient diameter to little more than readily slideably receive the plunger 43. The proximal end 61 of the hollow body element 41 that extends into the cap 40, that is, the face of the open upper end, must have sufficient wall thickness, or a suitable flange provided, to serve as a stop for the coil spring 54 to press against resiliently in urging the body element 41 outwardly of the telescoped position within the cap 40 when manual pressure on the closed end 44 of cap 40 is released.

This is necessary so that, as shown in FIG. 17A, the stylet 42 will be held far enough up the needle shaft for the loading of a T-fastener 48 in the slotted portion 53 of the needle 47 employed, with the T-fastener thrust into the needle with normally only half of the T-fastener visible in the slotted portion, the insertion stopping with the attached filament at the mid-length of the T-fastener at the closed end 49 of the slot.

Figure 13:
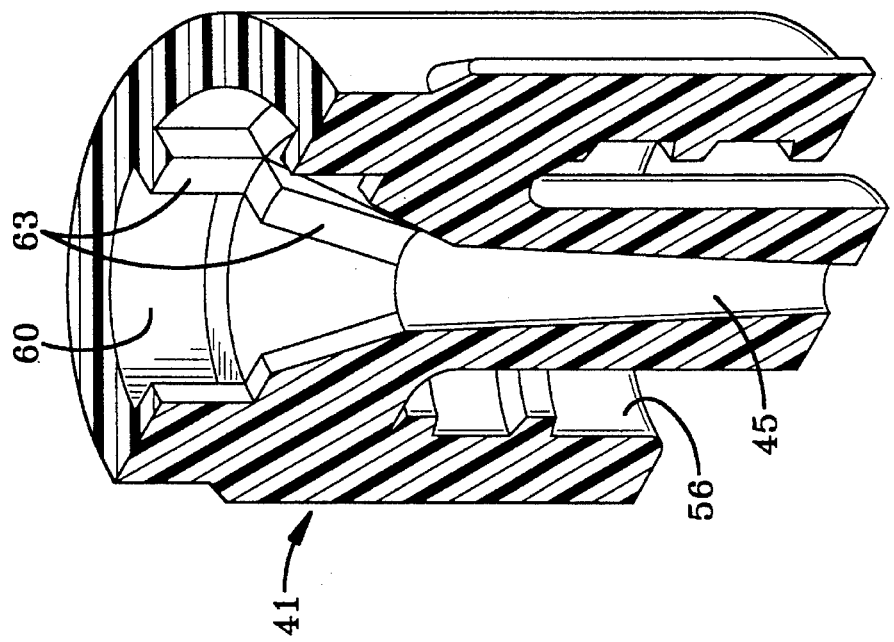
FIG. 13 is a perspective view in both transverse section and diametric section for purposes of illustration, being taken transversely a little above the conical narrowing of the cylindrical cavity of the body element, and, longitudinally along the diametric line of a perspective view of the body element as seen in FIG. 2, and rotated about one-eighth of a turn about its longitudinal axis.
Figure 12:
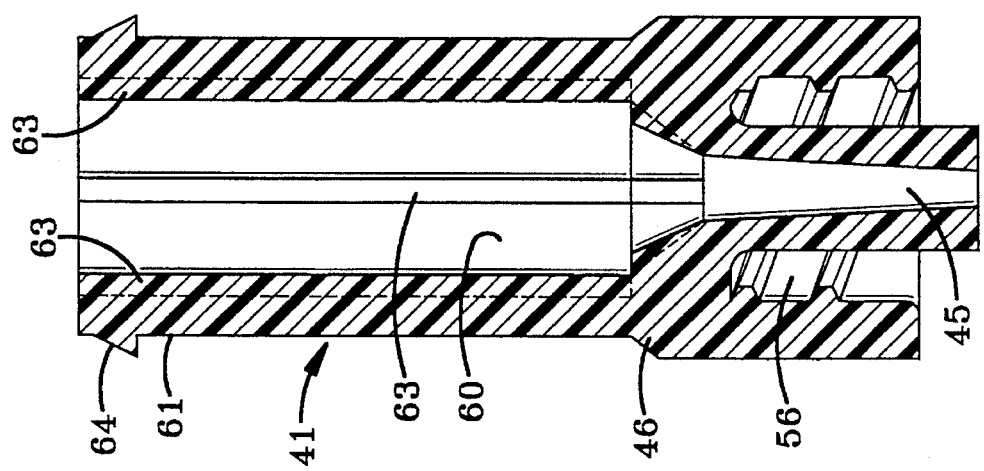
FIG. 12 is a view in diametric section taken longitudinally along line 12—12 of FIG. 10.
Figure 14:
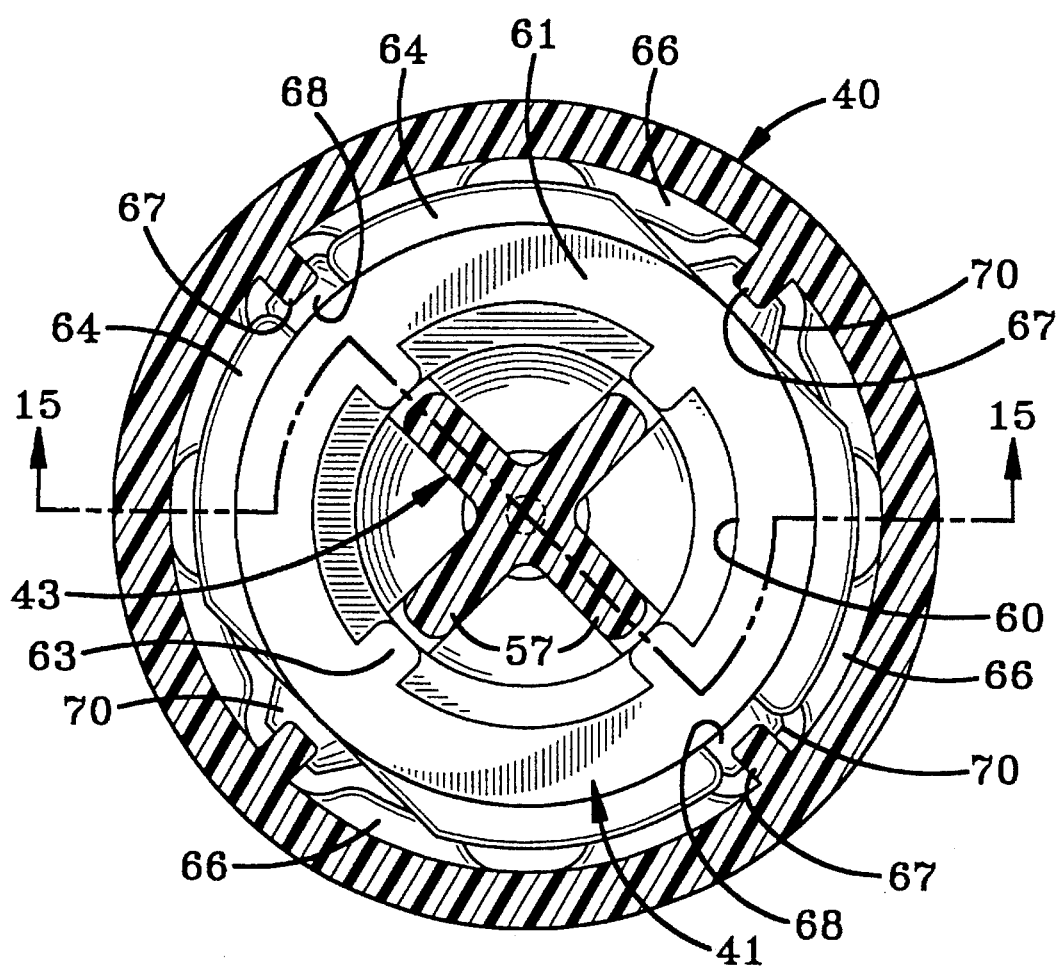
FIG. 14 is a greatly enlarged view in transverse section of the stylet holder assembly of FIG. 1, taken along line 14—14, with the coil spring that surrounds the plunger omitted for the sake of reducing the complexity of the view.

Turning to FIGS. 10, 12 and 13, a suitable stop may take the form of a set of radially inwardly extending ribs 63 on the inside of the body element 41. These ribs extend longitudinally from the proximal end 61 of the body element 41 down to about the substantially closed end 46 and serve also as guides for the plunger 43, meshing between the flanges 57 of the plunger 43 and acting as spacers between the plunger 43 and the body element 41. While three such ribs 63 about equally-spaced are adequate, four ribs, preferably about equally spaced, are more preferred for smooth operation.

Preferably, as shown in FIGS. 8–11, the body element 41 at its proximal end 61 is shaped with a peripheral annular ridge or boss 64 while the cap 40 at its open end 65, as shown in FIGS. 5, 6 and 7, is shaped with a radially inwardly extending annular ridge or boss 66. In order to be able to utilize these features cooperatively as a convenient means for retaining the upper end of the body element 41 at least slightly within the open, lower end of the cap 40, and still be able to assemble the parts together, it is essential that the inner diameter of the inward annular ridge 66 of the cap 40 be only slightly smaller than the outer diameter of the peripheral ridge 64, and that at least one of the annular ridges, and preferably both, be formed of resilient material, such as a synthetic polymeric resin, for example, an ABS resin of copolymerized acrylonitrile, butadiene and styrene. Assembly is further aided by interruptedly segmenting, and thus making discontinuous, at least one, but preferably both, annular ridges, reducing the stiffness of the ridges, as seen in the bottom view of the cap 40 in FIG. 5, and the bottom view of the body element 41 in FIG. 10. Beveling the peripheral ridge 64, whether segmented or not, to make it flared with the greater diameter away from the open end 61 of the body element as seen in FIGS. 2 and 8, also will ordinarily make assembly easier while still retaining resilient retentiveness, and disassembly possible with a rather slight amount of forcing. As seen in FIGS. 8 and 10, the ridge 64 may be omitted along portions of a pair of opposing sides of the body element, for example, along lines tangential to the sides as shown in the figures, thus further making assembly and disassembly easier, without eliminating the retentive action of the remainder of the ridge 64.

If desired, as shown in FIG. 5, the cap 40 may also be provided with several, preferably four, radially inwardly extending longitudinal ridges 67 that are best about equally spaced around the edge of the end of the cap and located between segments of the annular ridge 66, while the annular peripheral ridge 64 of the body element 41 is formed with complementary slots 68 therethrough. These structural features together provide for more stable, controllable uniform action in using the assembly to insert a needle into a hollow organ of a patient and then pressing the cap telescopically over the body element, ejecting a T-fastener from the needle and within the hollow organ.

In general, it is preferred that the parts be designed to utilize longitudinal ribs or ridges and segmentation thereof where appropriate in producing, e.g., cylindrical parts that will smoothly reciprocate telescopically, in accordance with good molding practice in the manufacture of plastic parts.

If desired, the closed end 44 of the cap 40 may be externally shaped concavely as seen in the top view in FIG. 4, for more comfortable retention of a finger tip on the cap during use. The periphery of the cap adjacent the closed end 44 may also be textured or grooved to make the cap easier to manipulate with gloved fingers. See, for example, the grooves 69 in FIGS. 1, 2 and 3.

Forming the body element 41 with short external longitudinal ribs 70 at the substantially closed end 46 is desirable in order to provide a stop for the telescopic motion of the cap 40 over the body element 41, and also to strengthen the structure of the luer lock fitting which is ordinarily used as the attachment means 56 for the needle 47 used for T-fastener emplacement. Referring now to FIGS. 12 and 13, forming the body element 41 with a cylindrical cavity 60 that converges conically at the substantially closed end 46 to a borehole 45 provides a further stop means that comes into effect if the plunger 43 reaches the conical portion, as illustrated in FIGS. 15 and 16.

In FIG. 17 there is illustrated an embodiment 39 of the stylet holder assembly of the invention ready for typical use with a slotted needle 47 attached and with a T-fastener 48 inserted in the slot 53 of the needle. The T-fastener has a filament 72 attached at its mid-length, and, threaded on the filament, ready for use, is a cotton pledger 73, a washer 74, and crimpable elements 75. The cotton pledger, washer and crimpable elements together serve as retaining means at the level of the external body surface of the patient for the filament under tension after the T-fastener has been emplaced and the hollow organ pulled into position internally against the body wall, e.g., the abdominal wall.

Figure 17B:
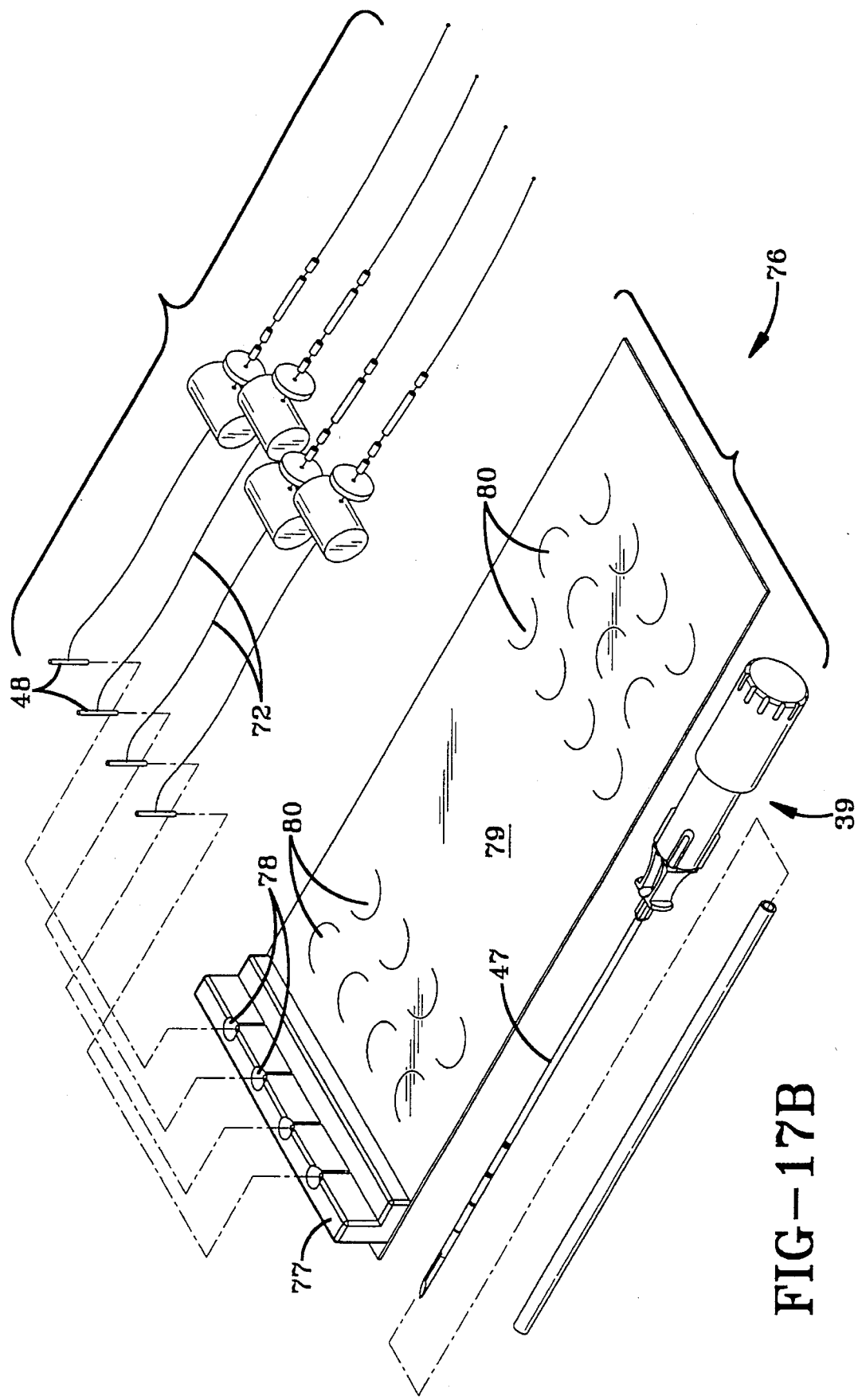
FIG. 17B is an exploded perspective view of a T-fastener installation kit of the type disclosed in U.S. Pat. No. 5,307,924 employing a stylet holder assembly of the present invention.
Figure 18:
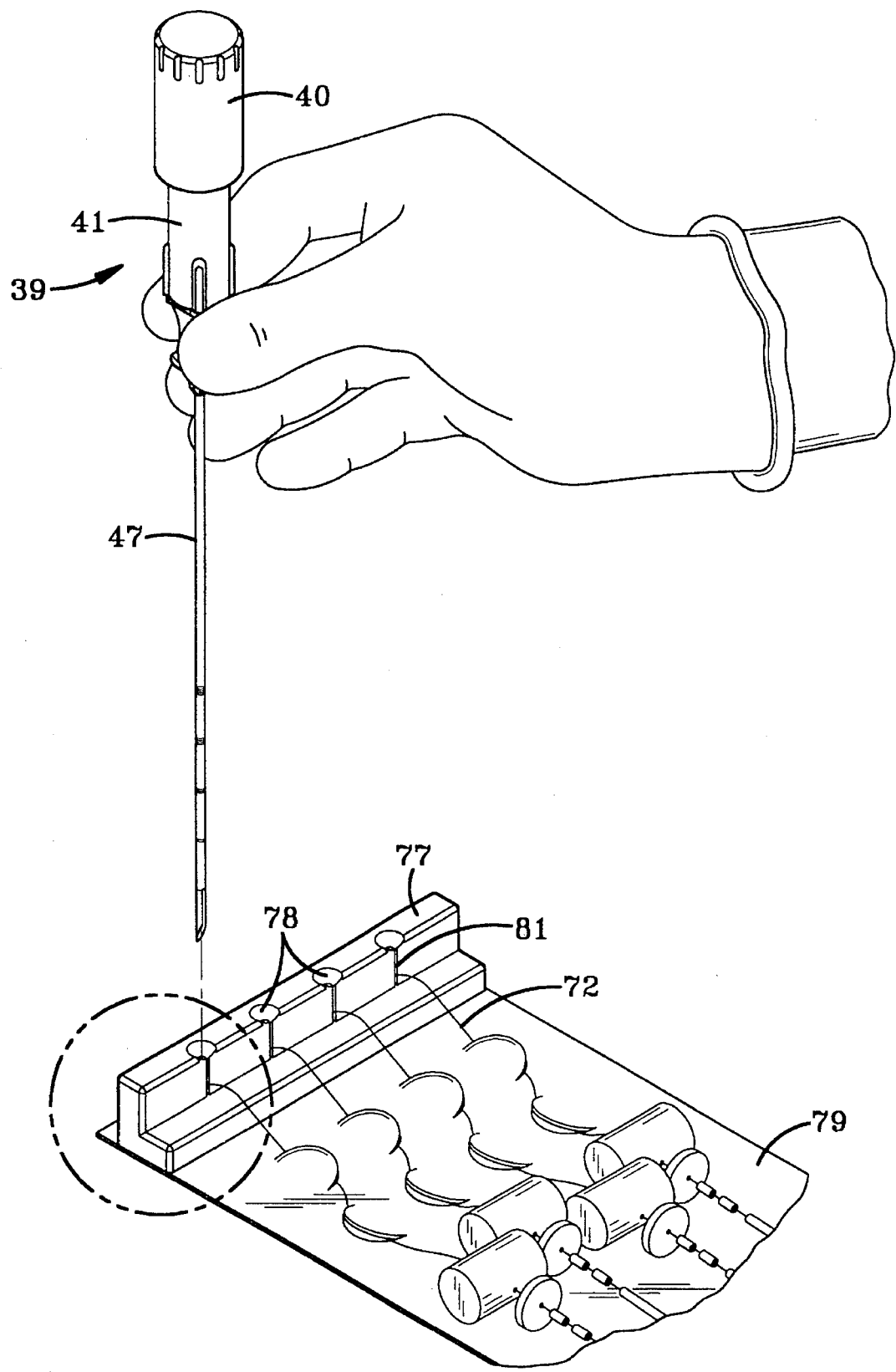
FIG. 18 is a perspective view of the stylet holder assembly of the invention with a slotted needle attached as the assembly is conveniently held in the hand of a surgeon, while the slotted needle is about to be loaded with a T-fastener from a loading block of a T-fastener installation kit.
Figure 19:
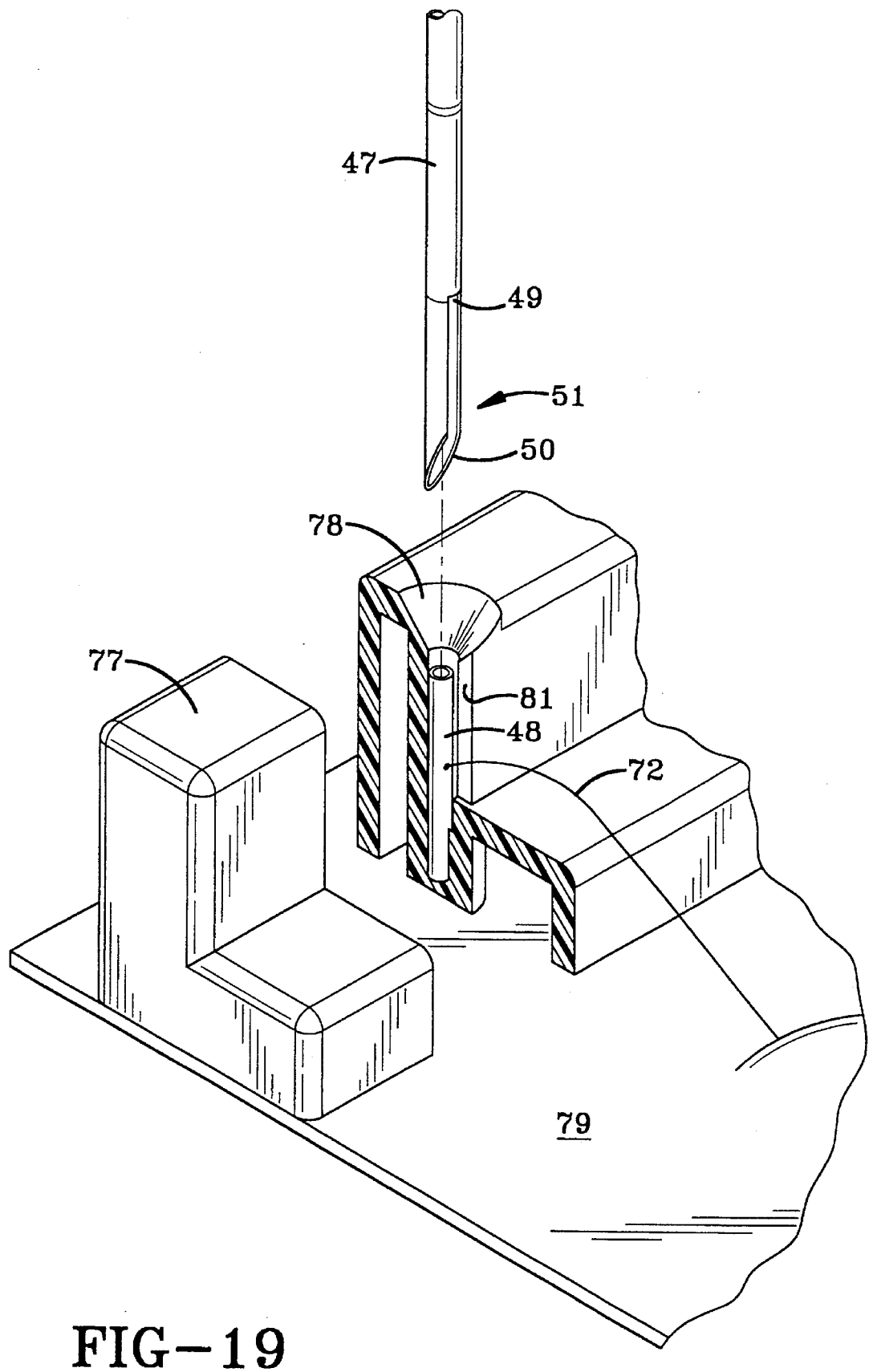
FIG. 19 is a greatly enlarged fragmentary detailed view of the encircled portion of FIG. 18, with a portion of the loading block cut away and removed, showing how the T-fastener is held in the loading block of the installation kit which guides the needle tip into proper position to receive the T-fastener with the attached filament extending out through the slot.
Figure 20:
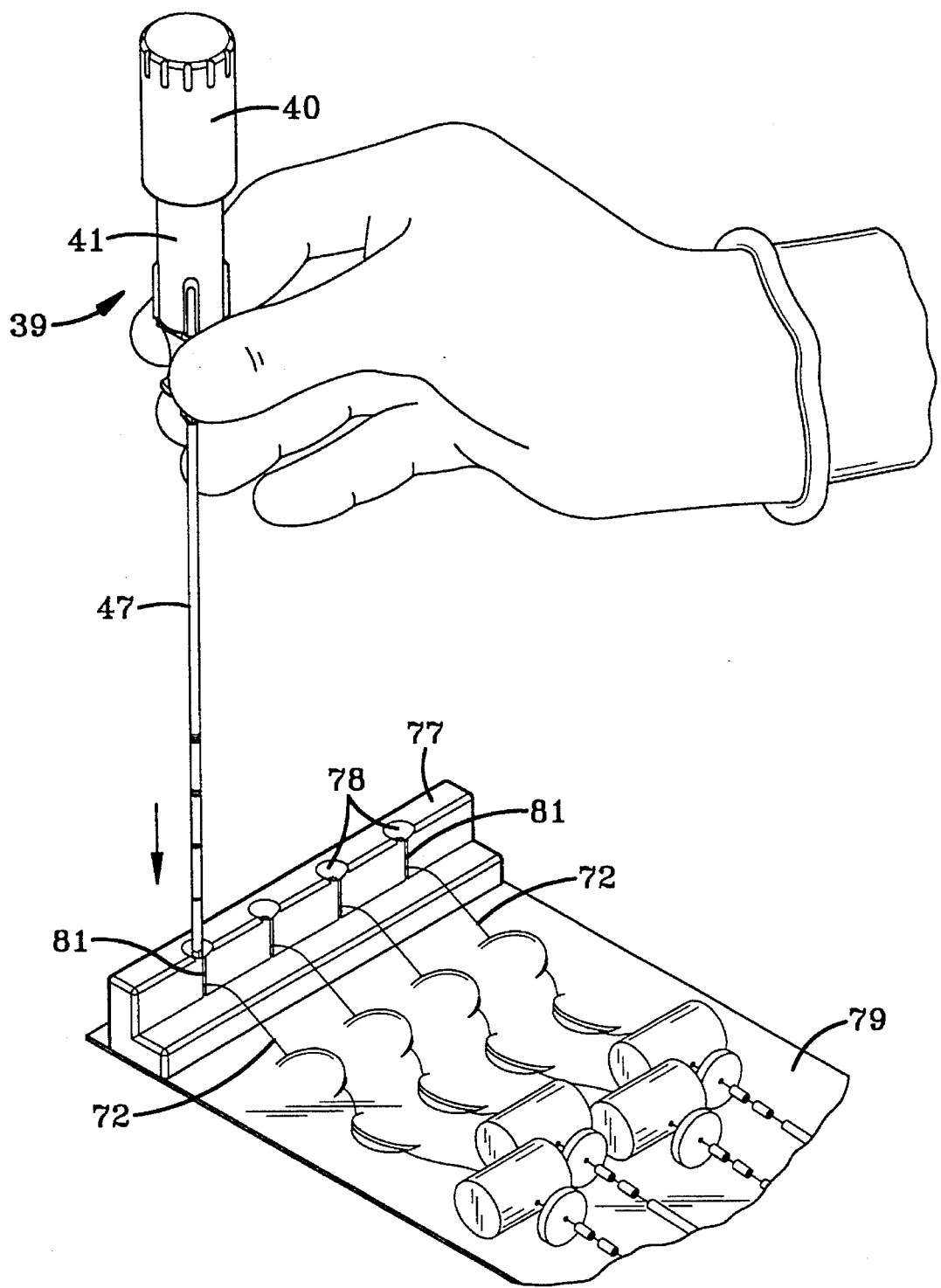
FIG. 20 is a view similar to FIG. 18 showing the stylet holder assembly of the invention with slotted needle attached and the needle tip inserted into the loading block during loading of a T-fastener.

The stylet holder assembly is conveniently readied using the kit of U.S. Pat. No. 5,307,924 which is depicted in FIG. 17B. The kit 76 consists of a block 77 with specially shaped cavities 78, each holding one T-fastener 48 in a vertical position such that it can be readily placed in the slotted portion 53 of the type needle 47 used for the purpose, so that the T-fastener 48 is positioned as shown in FIG. 17A, within the needle 47 with the T-fastener entirely above the beveled tip 51 of the needle and half of the T-fastener above the slotted portion 53. The kit also includes a suitable base layer or sheet 79, e.g., of heavy paper or of cardboard with flaps 80 formed thereof and raised sufficiently to serve as retaining or storage means for the filament 72 attached to each T-fastener and the retaining elements threaded thereon. In FIG. 19 there is shown the details of construction of a convenient form of a cavity 78 of the base or block 77 for positioning each T-fastener so that it will slide into the proper place in the slotted needle. The opening of the cavity 78 is countered to readily guide a needle tip thereunto, and the bottom of the cavity is stepped down to a smaller diameter to force the T-fastener up past the beveled tip of the needle into the slotted portion 53. A lateral slot 81 of the cavity 78 permits the filament 72 attached at mid-length of the T-fastener to extend laterally out of the way during positioning the T-fastener in the needle slot 53 as seen in FIGS. 18 and 20.

Figure 21:
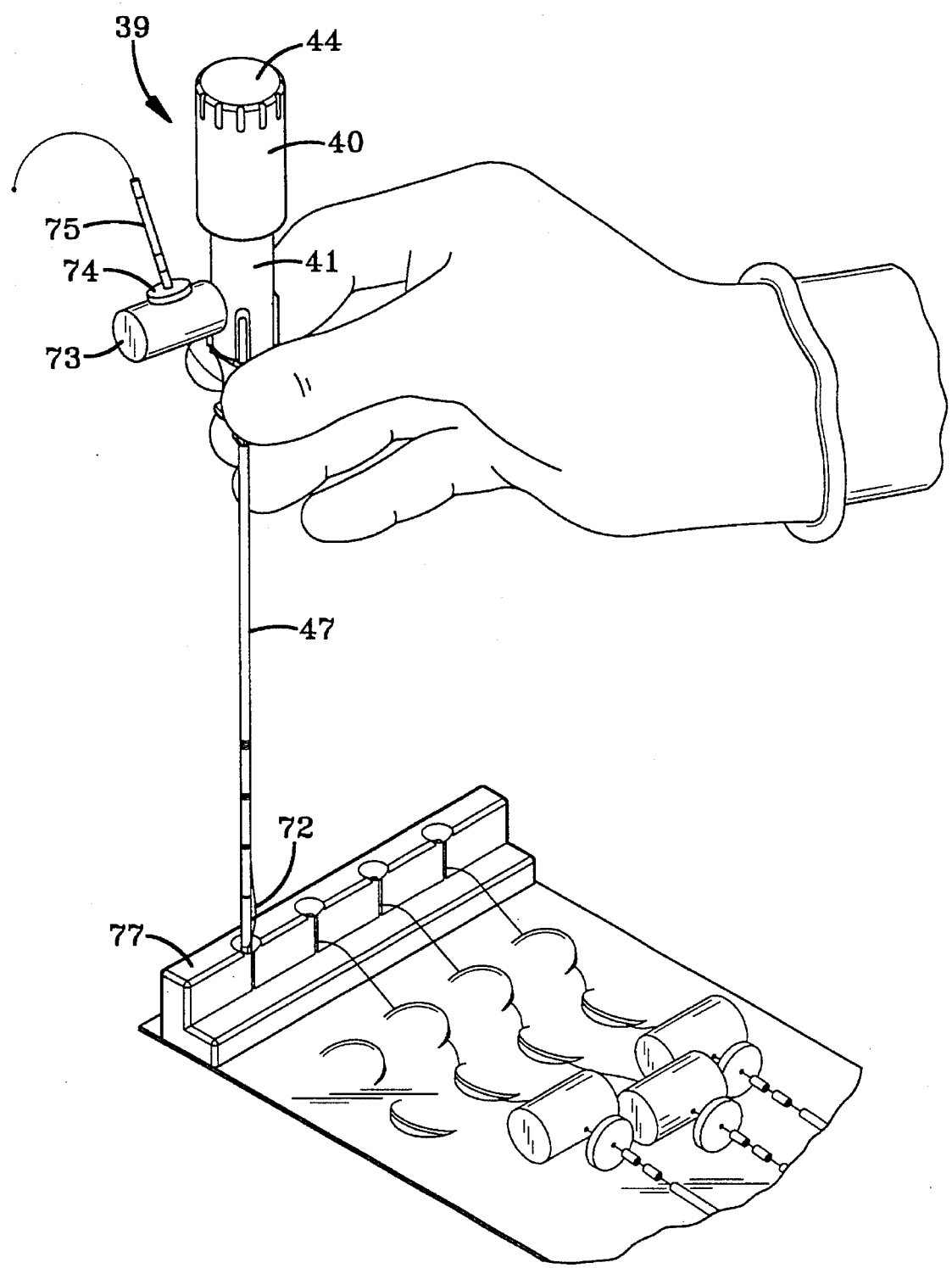
FIG. 21 is a view similar to FIG. 20 showing the T-fastener assembly, including the filament with the pledger, the washer and the crimping elements all threaded on the filament, as the T-fastener assembly is conveniently held by the same hand as the stylet holder assembly of the invention.
Figure 22:
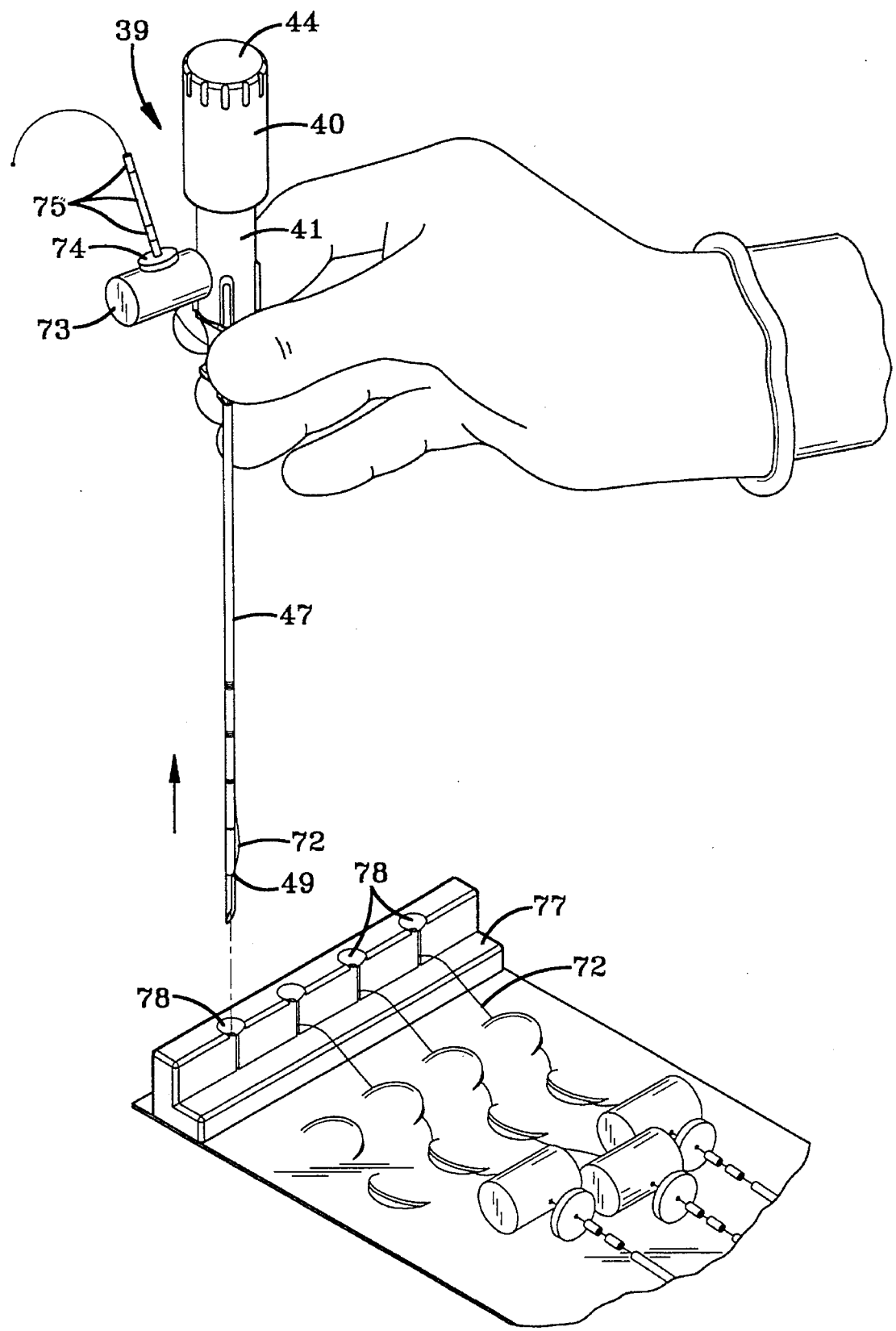
FIG. 22 is a view similar to FIG. 21 showing a T-fastener loaded into the slotted needle and the needle tip lifted away from the loading block and with the filament and the retaining elements grasped along with the stylet holder assembly.
Figure 23:
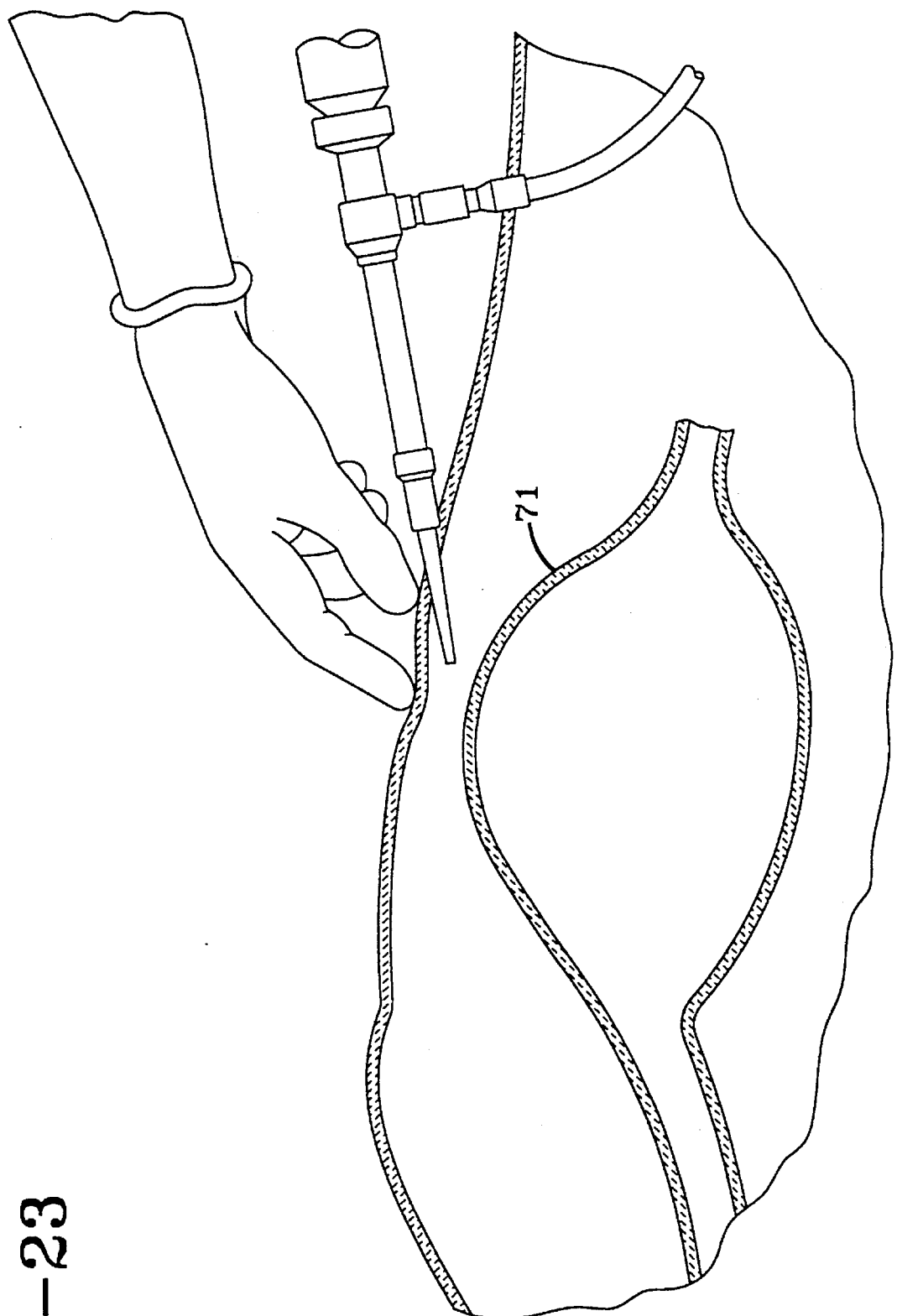
FIG. 23 shows the preparation for the emplacement of a T-fastener in a hollow organ of a patient, here the stomach, using a laparoscopic procedure for guidance, the body of the patient being shown in fragmentary sectional view.
Figure 24:
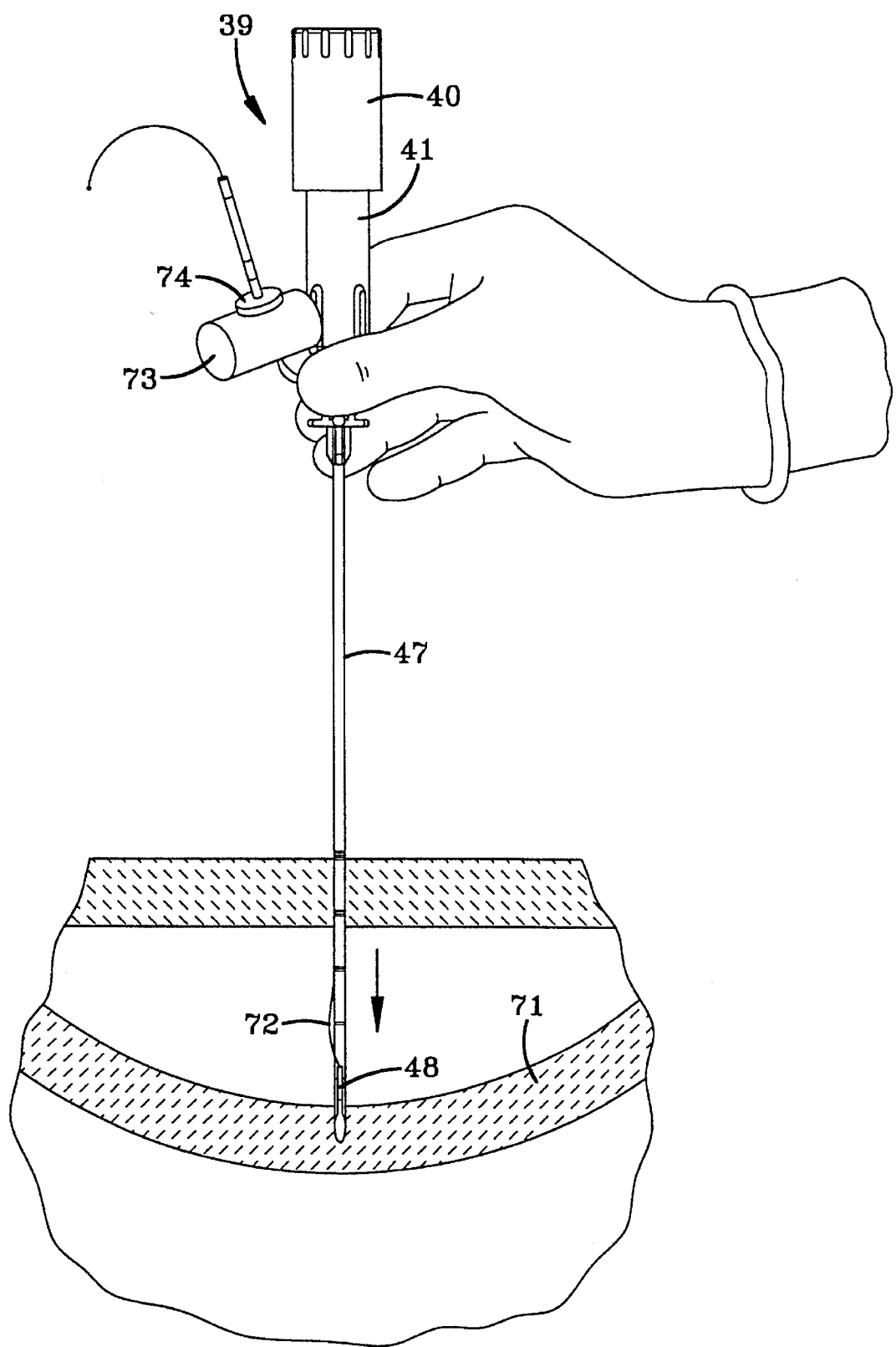
FIG. 24 is a view in section of a portion of the body parts as in FIG. 23 with the hand of a surgeon shown in full guiding the stylet holder assembly of the invention with slotted needle attached and loaded with a T-fastener with the T-fastener assembly attached thereto, the needle having been inserted through the abdominal wall, through the peritoneal cavity and into the wall of the hollow body organ, here the stomach.
Figure 25:
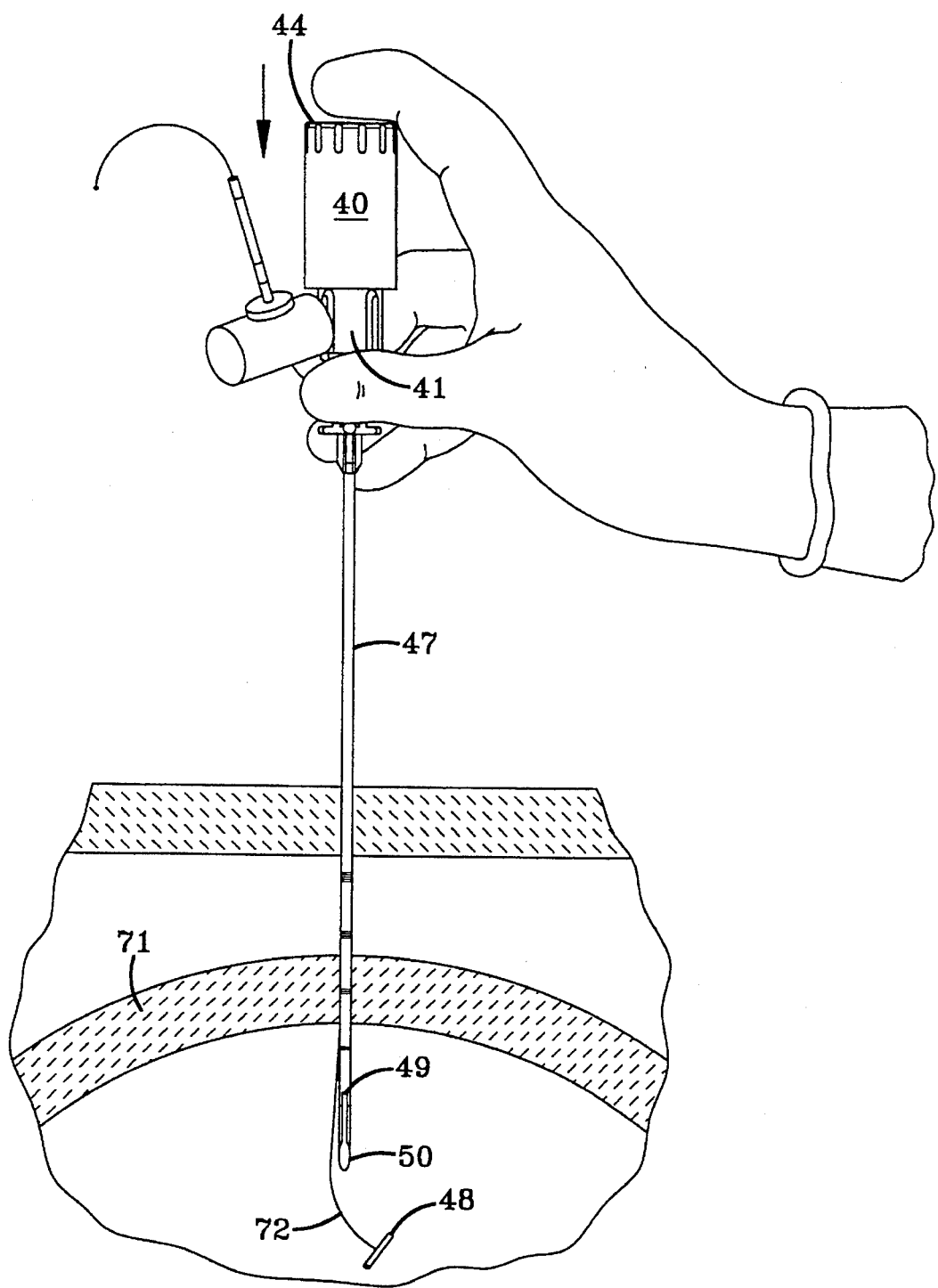
FIG. 25 is a view similar to FIG. 24 showing the needle of the assembly extending into the hollow organ and with the organ partially distended by insufflation while the cap of the stylet holder assembly has been pressed down over the body element by the index finger of the surgeon, causing the stylet to eject the T-fastener within the hollow organ.

After the T-fastener 48 is positioned or loaded in the needle 47, the filament 72 and retaining means 73,74,75 thereon are conveniently picked up and held with one hand by the surgeon, together with the stylet holder assembly 39 and needle 47 as seen in FIGS. 21 and 22. After the surgeon has laparascopically located the appropriate site for inserting a T-fastener into an insufflated hollow organ, such as the stomach 71 of a patient, as illustrated in FIG. 23, the stylet holder assembly 39, with attached needle 47 with T-fastener 48 loaded therein, is picked up together with the filament 72 and retaining elements, 73,74,75 and conveniently and controllably and confidently held with one hand by the surgeon and inserted into the hollow organ of the patient, as seen in FIG. 24. Then, the T-fastener 48 is simply and conveniently ejected inside the hollow organ by the surgeon pressing down on the closed top end 44 of the cap 40, as with the index finger, against the pressure of the coil spring 54 within the assembly 39, thus extending the stylet 42 further through the needle 47 to the beveled tip 50, whereupon the T-fastener 48 is ejected from the needle slot 53 in which it had been loaded, as depicted in FIG. 25.

Figure 26:
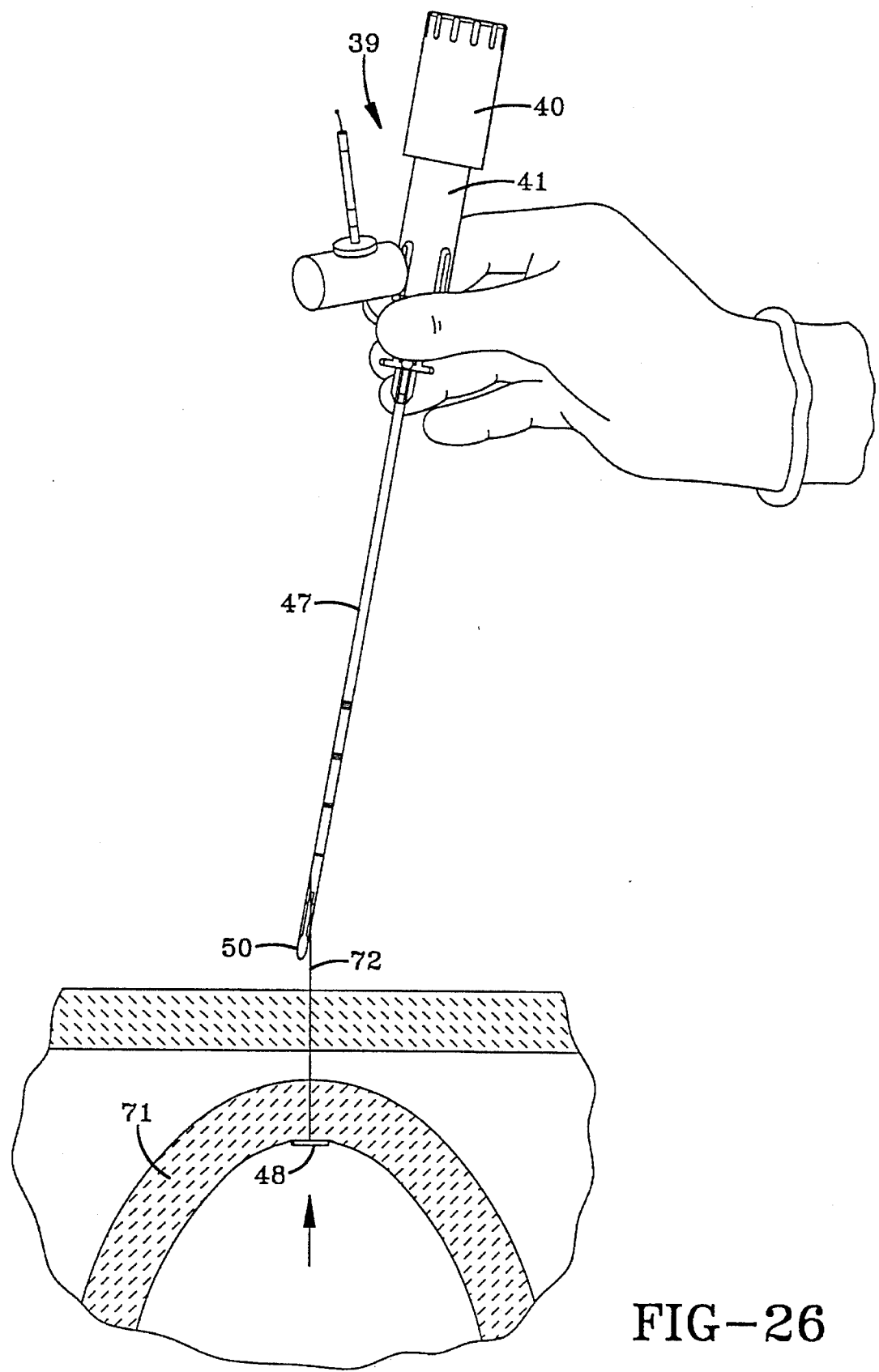
FIG. 26 is a view similar to FIG. 25 showing the cap of the stylet holder assembly released from compression against the coil spring and the hand of the surgeon pulling up on the stylet holder assembly and the filament of the T-fastener assembly, thus pulling the T-fastener into place, and further, as a consequence, pulling the wall of the hollow organ up towards the abdominal wall.
Figure 27:
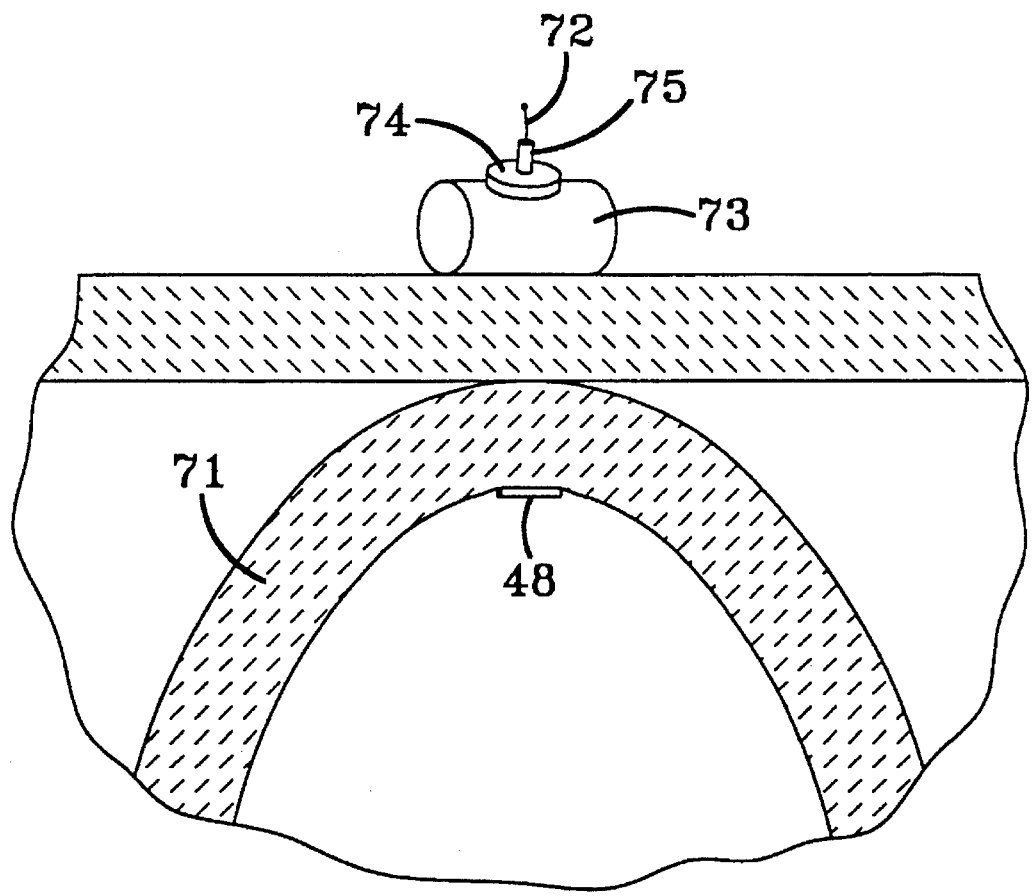
FIG. 27 is a fragmentary view of the body parts, somewhat similar to FIG. 26, showing the wall of the hollow organ snugged up against the abdominal wall with the T-fastener inside the hollow organ and the filament secured outside the abdominal wall with a pledget and washer and a crimping element around the end of the filament that has been trimmed back to the crimping element.

Thereafter, the stylet holder assembly 39 and the filament 72 together with the retaining elements 73,74,75 are withdrawn from the body of the patient and sufficient tension applied to the filament 72 to pull the T-fastener 48 and thus the wall of the hollow organ up toward the abdominal wall as shown in FIG. 26. After the wall of the hollow organ has been drawn up sufficiently with tension on the filament 72 pulling the T-fastener 48, and with the cotton pledget 73 firmly against the exterior of the abdominal wall, the washer 74 is pressed down against the pledget 73 and the crimpable element or elements 75 against the washer, and the crimpable elements crimped securing the filament 72, the unneeded tail of which is cut off, completing the T-fastener emplacement. Usually four of such T-fasteners are used, being placed at the corners of a square through which a feeding tube, e.g., is to be inserted.

In a useful modification of the assembly of the invention, as illustrated in FIGS. 28 and 29, an insufflation adapter, indicated generally by the numeral 90, having a hollow body 91 with attachment means 92,93 at respective ends, is attached to the body element 41 by engaging the attachment means 92 with the complementary interior surface defining attachment means cavity 56 within the substantially enclosed end 46 of the body element 41. See cavity 56 in FIGS. 15 and 16. The attachment means cavity 56 is normally a female luer lock fitting, as is the attachment means 93, while attachment means 92 is normally a male luer lock fitting.

The hollow body 91 of the insufflation adapter 90 is provided with a conventional hemostasis valve that bridges the passageway through the hollow body and controls movement of any fluid therethrough and the valve has a central perforation or borehole therethrough through which the stylet 42 slideably extends. A lateral fluid connection in the form of a "T" or side port 94 to the hollow body 91 connects to a short length of hollow tubing 95.

A hemostasis valve is a check valve consisting of a plurality of layers of thin flexible plastic disks bridging a valve body type passage and provided with sufficient axial compression to prevent flow therethrough of a fluid, such as a body fluid or gas. Nonetheless, the axial compression may be adjusted so that the central axial perforation here permits resilient movement of the stylet therethrough without passage also of fluid.

The plural layer hemostasis valve is located between the side port 94 and the attachment means 92 which connects to the attachment means cavity 56 of the body element 41. The valve is inside the threaded end of the hollow body 91 of the adapter and is surrounded by the nut 98 threaded onto the hollow body and attaching the male luer lock fitting 92. Nut 98 is integrally formed with and concentrically around the end of the tube 99 of the male luer lock fitting. The tube 99 is of a diameter to be slid into the hollow body 91. The end of the tube 99 is preferably provided with a slightly raised circumferential ridge, while the externally threaded end of the hollow body 91 is also provided with a slight internal annular ridge for resilient retention of the parts. Threading the nut 98 onto the hollow body 91 forces the end of the tube 99 inside the hollow body 91 against the hemostasis valve and tightening the nut 98 permits compression of the valve layers around the stylet, thus providing an adjustable degree of sealing and of ease of sliding the stylet.

At the end of the tubing 95 is a luer lock fitting 97 for connection with, e.g., a hypodermic syringe for the purpose of carrying out insufflation as may be indicated for the patient. The tubing is closed with a luer lock fitted cap 96 for positive closure when the syringe (not shown) is attached.

The foregoing embodiment of the assembly affords the carrying out of insufflation without having to disconnect the assembly and avoiding what may be awkward manipulations.

If desired, the substantially closed end 46a of the hollow body element 41a illustrated in the fragmentary view in FIG. 28A, may be internally threaded and the adapter body 91a threaded externally and complementarily thereto to provide a simple manner of connecting the adapter body 91a in the modified type of assembly corresponding to that shown in FIG. 28, for use in carrying out insufflation without having to disconnect the assembly in order to utilize a hypodermic syringe. As seen in the embodiment shown in fragmentary view in FIG. 24, the substantially closed end 46a of a body element 41a may be internally threaded, instead of being formed with a male luer lock fitting that normally receives the base of the needle. An insufflation adapter corresponding to adapter 90 in FIG. 29 has a hollow body 91a with an externally threaded connector end 92a which threadably engages the closed end 46a. The other end of the insufflation adapter carries a male luer lock fitting 93a, while a sideport 94a extends from the side of the hollow body 91a and is connectable by means of tubing 95a, if desired, to means such as a luer lock fitting as shown in FIG. 29, for attaching the device to a hypodermic syringe for carrying out insufflation without having to disconnect the stylet holder.

Figure 30:
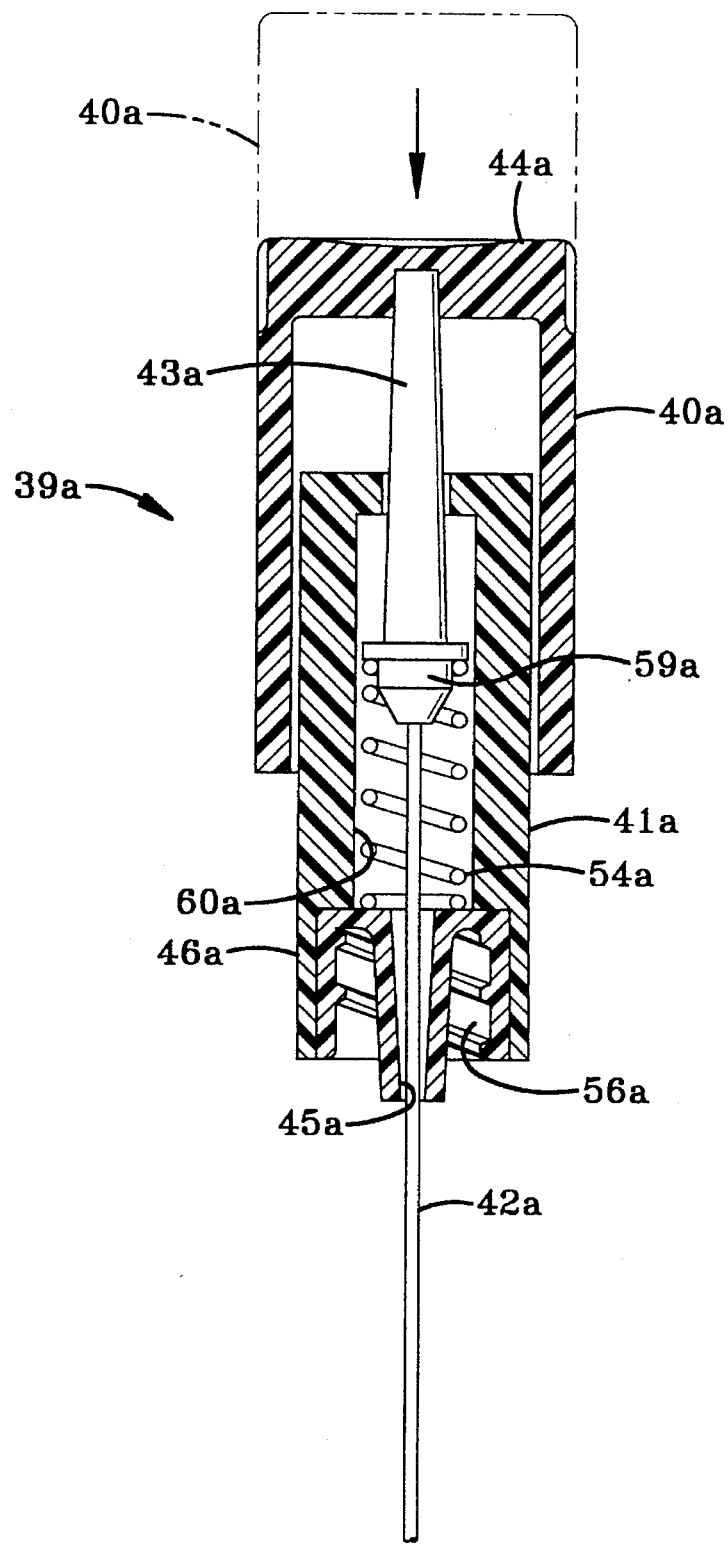
FIG. 30 is a view in section of another embodiment of the stylet holder assembly of the invention in which the coil spring that urges the body element outwardly of the cap is positioned inside the body element instead of inside the cap. In the assembly shown, the cap has been pressed down, telescoping part way over the body element and thus extending the stylet further out through the borehole in the substantially closed end of the body element. The normal return position of the cap when released is indicated in dotted outline.

In another embodiment of the stylet holder assembly of the invention seen in FIG. 30, the coil spring urging the body element out of the cap is positioned within the body element instead of on top of it, that is, at one end of it, and bears against the bottom of the cavity of the body element instead of against the top rim of the body element. The coil spring also bears against the distal end of the plunger instead of the closed end of the cap, and is not positioned within the cap, except to the extent the plunger is telescoped within the cap.

Turning now to FIG. 30, the stylet holder assembly, referred to generally as 39a, is seen to have a cap 40a with a plunger 43a depending from the closed end 44a thereof. The plunger 43a is nested within the cylindrical cavity 60a of the hollow body element 41a, while the hollow body element 41a extends telescopically into the cap 40a. A coil spring 54a bears against the distal end of the cavity 60a adjacent the substantially closed end 46a of the body element, and oppositely against the lower or distal end 59a of the plunger 43a. A stylet 42a is attached to the distal end 59a of the plunger 43a and extends freely slideable through a small borehole 45a in the substantially closed end 46a of the body element 41a. The substantially closed end 46a of the body element 41a is shaped as a female luer lock fitting 56a. Without the complexity of the annular and peripheral ridges and longitudinal ribs of the cap and the body element described above, the parts are somewhat easier to mold, though not as smooth and reliable acting in operation.

Among the advantages of the stylet holder assembly of the invention are the ease and simplicity of handling and the comfortable control by the user resulting in considerable peace of mind when approaching the procedure in which the assembly is used.

We claim:

1. A method of controllably holding and ejecting a T-fastener from a hypodermic needle tip during placement in a hollow organ of a patient comprising the steps of:

(a) providing an assembly of a spring-loaded reciprocable stylet holder comprising:

a cap having a closed end and an open end and a longitudinal axis;

a hollow body element having a longitudinal axis and an open end portion partially nested within and reciprocable partially into the cap, and an opposite end that is substantially closed, having a borehole therethrough, the longitudinal axes of the cap and body element being coincidental;

a spring within the stylet holder assembly urging the body element outwardly of the cap;

a stylet supported at one end thereof by and within the cap and along the longitudinal axis thereof, the stylet slideably extending through and beyond a borehole in the substantially closed end of the body element along the longitudinal axis thereof;

the substantially closed end of the body element having means for attaching a hypodermic needle thereto so as to telescopically cover with the hypodermic needle the portion of the stylet extending beyond the substantially closed end of the body element; and a hypodermic needle held by the attachment means with the stylet extending therethrough to adjacent the tip thereof, the needle being of the requisite gauge and length for insertion of a T-fastener within a hollow organ of a patient and having a slotted tip portion to slideably receive and hold a T-fastener;

(b) placing a T-fastener with an attached filament within the slot of the needle with the distal end of the stylet resting within the needle closely adjacent the T-fastener;

(c) inserting the needle into a hollow organ of the patient at a pre-selected site;

(d) sufficiently pressing down the cap of the stylet holder over the body element and against the urging of the spring within the stylet holder to move the stylet to eject the T-fastener from the tip of the needle; and (e) releasing the cap to allow the spring to urge the cap, stylet and body element back in the opposite direction to the original position of each element.

2. The method of claim 1 further comprising the step of:

(f) withdrawing the assembly of the stylet holder and the needle from the body of the patient.

* * * * *